US008364217B2

(12) United States Patent
Ballerstadt et al.

(10) Patent No.: US 8,364,217 B2
(45) Date of Patent: *Jan. 29, 2013

(54) SYSTEM, DEVICE AND METHOD FOR DETERMINING THE CONCENTRATION OF AN ANALYTE

(75) Inventors: Ralph Ballerstadt, Houston, TX (US); Roger McNichols, Pearland, TX (US); Ashok Gowda, Houston, TX (US)

(73) Assignee: BioTex, Inc., Houston, TX (US)

( * ) Notice: Subject to any disclaimer, the term of this patent is extended or adjusted under 35 U.S.C. 154(b) by 1619 days.

This patent is subject to a terminal disclaimer.

(21) Appl. No.: 11/811,083

(22) Filed: Jun. 8, 2007

(65) Prior Publication Data

US 2007/0249917 A1    Oct. 25, 2007

Related U.S. Application Data

(63) Continuation of application No. 10/929,056, filed on Aug. 27, 2004, now Pat. No. 7,236,812.

(60) Provisional application No. 60/499,495, filed on Sep. 2, 2003.

(51) Int. Cl.
    *A61B 5/1455* (2006.01)
(52) U.S. Cl. ........................................ 600/316; 600/310
(58) Field of Classification Search ................. 600/310, 600/316, 322, 341, 365, 473, 476; 422/82.05, 422/82.06; 436/95, 805
See application file for complete search history.

(56) References Cited

U.S. PATENT DOCUMENTS

| 4,041,932 A | 8/1977 | Fostick |
| 4,071,020 A | 1/1978 | Pugliese |
| 4,261,968 A | 4/1981 | Ullman et al. |
| 4,330,299 A | 5/1982 | Cerami |
| 4,344,438 A | 8/1982 | Schultz |
| 4,401,122 A | 8/1983 | Clark, Jr. |

(Continued)

FOREIGN PATENT DOCUMENTS

WO    WO 00/64492    11/2000

OTHER PUBLICATIONS

"Fiber-Optic Biosensors Based on Fluorescence Energy Transfer", Meadows et al., Talents, vol. 35, No. 2, pp. 145-150, (1988).

(Continued)

*Primary Examiner* — Eric Winakur
*Assistant Examiner* — Chu Chuan (JJ) Liu
(74) *Attorney, Agent, or Firm* — Quan & Associates; Nancy N. Quan

(57) ABSTRACT

There are many inventions described and illustrated herein. In one aspect, the present invention is a system, a device and a method for sensing the concentration of an analyte in a fluid (for example, a fluid sample) or matrix. The analyte may be glucose or other chemical of interest. The fluid or matrix may be, for example, the fluid or matrix in the body of an animal (for example, human), or any other suitable fluid or matrix in which it is desired to know the concentration of an analyte. In one embodiment, the invention is a system and/or device that includes one or more layers having a plurality of analyte-equivalents and mobile or fixed receptor molecules with specific binding sites for the analyte-equivalents and analytes under analysis (for example, glucose). The receptor molecules, when exposed to or in the presence of analyte (that resides, for example, in a fluid in an animal), bind with the analyte (or vice versa). As such, some or all (or substantially all) of the receptor molecules within a given layer may bind with the analyte, which results in a change in the optical properties of one or more of the layers. These layer(s) may be examined or interrogated, via optical techniques, whereby the optical response of the layers and/or, in particular, the substance within the layer(s), may be measured, evaluated and/or analyzed.

41 Claims, 17 Drawing Sheets

U.S. PATENT DOCUMENTS

| | | | |
|---|---|---|---|
| 4,450,104 A | 5/1984 | Jordan | |
| 4,868,103 A | 9/1989 | Stavrianopoulos et al. | |
| 4,981,779 A | 1/1991 | Wagner | |
| 5,001,051 A | 3/1991 | Miller et al. | |
| 5,028,787 A | 7/1991 | Rosenthal et al. | |
| 5,101,814 A | 4/1992 | Palti | |
| 5,143,066 A | 9/1992 | Komives et al. | |
| 5,244,636 A | 9/1993 | Walt et al. | |
| 5,320,814 A | 6/1994 | Walt et al. | |
| 5,321,501 A | 6/1994 | Swanson et al. | |
| 5,326,531 A | 7/1994 | Hahn et al. | |
| 5,341,805 A | 8/1994 | Stavridi et al. | |
| 5,342,789 A | 8/1994 | Chick et al. | |
| 5,459,570 A | 10/1995 | Swanson et al. | |
| 5,460,971 A | 10/1995 | Gottlieb | |
| 5,654,419 A | 8/1997 | Mathies et al. | |
| 5,780,247 A | 7/1998 | Satomura et al. | |
| 5,814,449 A | 9/1998 | Schultz et al. | |
| 6,040,194 A | 3/2000 | Chick et al. | |
| 6,210,326 B1 | 4/2001 | Ehwald | |
| 6,256,522 B1 | 7/2001 | Schultz | |
| 6,267,002 B1 | 7/2001 | Ehwald et al. | |
| 6,330,464 B1 * | 12/2001 | Colvin et al. | 600/316 |
| 6,383,767 B1 | 5/2002 | Polak | |
| 6,477,891 B2 | 11/2002 | Ehwald et al. | |
| 6,485,703 B1 | 11/2002 | Cote et al. | |
| 6,694,158 B2 | 2/2004 | Polak | |
| 6,725,073 B1 | 4/2004 | Motamedi et al. | |
| 6,846,638 B2 | 1/2005 | Shipwash | |
| 2001/0035047 A1 | 11/2001 | Ehwald et al. | |
| 2001/0045122 A1 | 11/2001 | Ehwald et al. | |
| 2002/0087145 A1 | 7/2002 | Ehwald et al. | |
| 2003/0049625 A1 | 3/2003 | Heyduk | |
| 2003/0054560 A1 | 3/2003 | Ehwald et al. | |
| 2003/0059811 A1 | 3/2003 | Djaballah et al. | |
| 2003/0228682 A1 | 12/2003 | Lakowicz et al. | |

OTHER PUBLICATIONS

"Chemiluminscent and Fluorescent Probes for DNA Hybridization Systems", Heller et al., DNA Hybridization Systems, pp. 245-257 (1985).

"Detection of Nucleic Acid Hybridization by Nonradiative Fluorescence Resonance Energy Transfer", Cardullo et al., Proc. Natl. Mad. Sci. U.S.A., vol. 85, pp. 8790-8794, Dec. 1988.

"Affinity Sensor: A New Technique for Developing Implantable Sensors for Glucose and Other Metabolites", Schultz et al., Diabetes Care, vol. 5, No. 3, pp. 245-253 (1982).

"A Fluorescence Affinity Hollow Fiber Sensor for Continuous Transdermal Glucose Monitoring", Ballerstadt et el., Analytical Chemistry, vol. 72, No. 17, (2000), pp. 4182-4192.

"Precision measurement of tissue optical properties with optical coherence tomography", Kholodnykh, et al., Applied Optics, (Jun. 1, 2003), vol. 42, No. 16, pp. 3027-3037.

"Noninvasive blood glucose monitoring with optical coherence tomography", Larin, et al., Diabetes Care, vol. 25, No. 12, (Dec. 2002). pp. 2263-2267.

"Protein-Carbohydrate Interaction", Poretz et al., Biochemical Pharmacology, vol. 20, pp. 2727-2739, Pergamon Press, (1971).

"Protein-Carbohydrate Interaction. II. Inhibition Studies on the Interaction of Concanavalin A with Polysaccharides", Goldstein et al., Biochemistry, vol. 4, No. 5, (May 1965), pp. 876-883.

\* cited by examiner

SYSTEM, DEVICE AND METHOD FOR DETERMINING THE CONCENTRATION OF AN ANALYTE

RELATED APPLICATIONS

This application is a continuation of application Ser. No. 10/929,056, now U.S. Pat. No. 7,236,812, filed August 27, 2004, the contents of which are incorporated herein by reference.

CROSS-REFERENCE TO RELATED APPLICATIONS

This application claims priority to U.S. Provisional Application Ser. No. 60/499,495, entitled "System, Device and Method for Determining the Concentration of an Analyte", filed Sep. 2, 2003. The contents of this provisional application are incorporated by reference herein in its entirety.

BACKGROUND OF THE INVENTION

1. Field of Invention

This invention is directed to a method and an apparatus to facilitate minimally invasive measurement, sampling and/or sensing of analytes, for example, glucose, in a fluid, matrix or animal body.

2. Description of the Related Art

Glucose sensing is an important diagnostic tool in therapy and research of diabetes mellitus as well as in cell culture and on-line process control in agricultural applications. Diabetes is a chronic systemic disease characterized by disorders in the metabolism of insulin, carbohydrate, fat, and protein as well as in the structure and function of blood vessels. Currently, diabetes is a leading cause of death in the United States, and more than sixteen million Americans are believed to have this disease. Intensive management of blood sugars through frequent monitoring is effective to prevent, or at least manage, the progression of diabetic complications such as kidney failure, heart disease, gangrene, and blindness.

Maintaining blood glucose levels near normal levels is typically achieved by frequently monitoring the blood glucose. Currently, the most common method of sensing is a colorimetric/electro-enzymatic approach, which is an invasive technique. In short, the colorimetric/electro-enzymatic approach requires blood to be drawn and tested. This often requires a finger stick to draw blood each time a reading is needed. In sum, this approach is typically time-consuming and often quite painful.

Minimally invasive approaches based on needle-type enzyme sensors (e.g., glucose oxidase) have been investigated as a less painful method of estimating and/or indirectly measuring blood glucose concentrations. Such approaches, however, have well-known limitations regarding measurement of glucose in interstitial fluid. For example, such approaches often suffer from a limitation on the accuracy and stability of the glucose measurement. In this regard, the chemical instability and/or external biocompatibility issues tend to adversely affect the signal sensitivity and stability of the sensor over time. Further, such techniques often require transcutaneous placement of the sensor which may be inconvenient, uncomfortable, a potential source of infection that may ultimately lead to a limitation on the maximum useful lifetime for the sensor. As such, there exists a need for a non-invasive or minimally invasive approach that overcomes one, some or all of the well-known limitations.

SUMMARY OF THE INVENTION

There are many inventions described and illustrated herein. In one aspect, the present invention is a system, a device and a method for sensing the concentration of an analyte in a fluid (for example, a fluid sample) or matrix. The analyte may be glucose or other chemical of interest. The fluid or matrix may be, for example, the fluid or matrix in the body of an animal (for example, human), or any other suitable fluid or matrix in which it is desired to know the concentration of an analyte.

In one embodiment, the invention is a system and/or device that includes one or more layers having a plurality of analyte-equivalents and mobile or fixed receptor molecules with specific binding sites for the analyte-equivalents and analytes under analysis (for example, glucose). The receptor molecules, when exposed to or in the presence of analyte (that resides, for example, in a fluid in an animal), bind with the analyte (or vice versa). As such, some or all (or substantially all) of the receptor molecules within a given layer may bind with the analyte, which results in a change in the optical properties of one or more of the layers. These layer(s) may be examined or interrogated, via optical techniques, whereby the optical response of the layers and/or, in particular, the substance within the layer(s), may be measured, evaluated and/or analyzed.

The degree to which such binding takes place is dependent upon, among other things, the concentration of analyte in, for example, the fluid or matrix in the body of an animal. Thus, the concentration of analyte may be determined by measuring, evaluating and/or analyzing the optical response of the layer(s). That is, in one embodiment, the concentration of the analyte may be determined by optically interrogating the layer(s), determining one or more optical properties of the layer(s) (and/or the constituents thereof), and analyzing or relating the one or more optical properties of the layer(s) to an analyte concentration.

In one principal aspect, the present invention is an analyte sensing device for sensing a concentration of analyte in a fluid. The analyte sensing device of this aspect includes a first sensor layer having at least one optical property (for example, transmission and/or scattering of optical radiation incident on the first sensor layer) that is responsive to the concentration of analyte in communication therewith. The first sensor layer includes a matrix, having a plurality of first analyte equivalent residues disposed therein, and a plurality of first analyte binding receptor molecules. The first analyte binding receptor molecules are capable of reversibly binding with the first analyte equivalent residues and the analyte.

The analyte sensing device may include a housing having a portion of the housing that is permeable to the analyte and non-permeable to the first sensor layer. The housing may also include a portion that is non-permeable to the analyte. In these embodiments, the first sensor layer is contained within the housing.

Notably, the first sensor layer may further include at least one extra-matrix space disposed between the matrix and the housing.

In one embodiment, the analyte sensing device further includes a second sensor layer having at least one optical property that is responsive to the concentration of analyte in communication therewith. The second sensor layer includes a matrix having a plurality of second analyte equivalent residues disposed therein and a plurality of second analyte binding receptor molecules. The second analyte binding receptor molecules are capable of reversibly binding with the second analyte equivalent residues and the analyte.

The analyte sensing device, in one embodiment, may also include a first target (for example, a reflective target or a fluorescent target) disposed within a path of optical radiation wherein the path of optical radiation also includes the first sensor layer. In another embodiment, the analyte sensing device also includes a second target wherein the second target is not in the path of optical radiation.

In one embodiment, the first analyte equivalent residues are confined within the matrix, and the first analyte binding receptor molecules are capable of migrating outside of the matrix. In another embodiment, the first analyte binding receptor molecules are confined within the matrix, and the first analyte equivalent residues are capable of migrating outside of the matrix.

The analyte sensing device may also include a plurality of nanoparticles. The nanoparticles may be attached to the first analyte binding receptor molecule and/or the first analyte equivalent residues.

Notably, the first sensor layer may be disposed around at least one fiber optic which is capable of providing radiation to and/or receiving radiation from the first sensor layer.

In another principal aspect, the present invention is an analyte sensing device for sensing a concentration of analyte in a fluid of an animal body. In this aspect, the analyte sensing device is capable of being implanted in the animal body such that it is in communication with the fluid. The analyte sensing device includes a sensor layer having at least one optical property that is responsive to the concentration of analyte in communication therewith. The sensor layer includes a matrix, having a plurality of analyte equivalent residues disposed therein, at least one extra-matrix space disposed between the matrix, and a plurality of analyte binding receptor molecules. The analyte binding receptor molecules are capable of reversibly binding with the analyte equivalent residues and the analyte.

The analyte sensing device of this aspect of the invention further includes a housing (for example, a permeable membrane that is permeable to analyte and non-permeable to the sensor layer), wherein the sensor layer is disposed within the housing. Notably, the at least one extra-matrix space is disposed between the matrix and the housing.

In one embodiment, the analyte equivalent residues are confined within the matrix, and the analyte binding receptor molecules are capable of migrating outside of the matrix. In another embodiment, the analyte binding receptor molecules are confined within the matrix, and the analyte equivalent residues are capable of migrating outside of the matrix.

Notably, the at least one optical property of the sensor layer may be a transmission and/or scattering of optical radiation incident on the sensor layer. Moreover, in at least one embodiment, the analyte is glucose, and the analyte sensing device is a glucose sensing device.

In another principal aspect, the present invention is a method to detect the concentration of an analyte in a fluid using an analyte sensing device. The analyte sensing device includes a sensor layer disposed within the housing, wherein the sensor layer exhibits at least one optical property that is responsive to the concentration of analyte in communication therewith. The sensor layer includes a matrix, having a plurality of analyte equivalent residues disposed therein, and a plurality of analyte binding receptor molecules, wherein the analyte binding receptor molecules are capable of reversibly binding with the analyte equivalent residues and the analyte.

The method includes placing an analyte sensing device in communication with the fluid and thereafter providing incident optical radiation to the analyte sensing device (for example, by providing incident optical radiation using an optical coherence tomography instrument). The method further includes receiving responsive optical radiation from the analyte sensing device and determining the concentration of analyte using the responsive optical radiation.

In one embodiment, the method further includes analyzing the responsive optical radiation to determine a change in transmission and/or scattering of optical radiation by the sensor layer. The analysis of the responsive optical radiation may include using a mathematical analysis of one or more optical coherence tomography return signals of the responsive optical radiation.

Again, there are many inventions, and aspects of the inventions, described and illustrated herein. This Summary of the Invention is not exhaustive of the scope of the present invention. Moreover, this Summary is not intended to be limiting of the invention and should not be interpreted in that manner. While certain embodiments, features, attributes and advantages of the inventions have been described in this Summary, it should be understood that many others, as well as different and/or similar embodiments, features, attributes and/or advantages of the present inventions, which are apparent from the description, illustrations and claims, which follow

BRIEF DESCRIPTION OF DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. Various combinations of the structures, components, materials and/or elements, other than those specifically shown, are contemplated and are within the scope of the present invention.

FIG. 8 illustrates OCT depth scans through layer with low turbidity (left) and layer with high turbidity (right); the difference in intensity of front and back return signals is a measure of attenuation within the layer and, hence, turbidity;

DETAILED DISCUSSION

There are many inventions described and illustrated herein. In one aspect, the present invention is a system, a device and a technique for sensing the concentration of an analyte (for example, glucose) in a fluid (for example, a fluid sample) or matrix in or from the body of an animal (for example, human). In one embodiment, the system and/or device includes one or more layers having a plurality of analyte-equivalents and mobile receptor molecules with specific binding sites for the analyte-equivalents and analytes under analysis (for example, glucose). The receptor molecules, when exposed to or in the presence of analyte (that resides, for example, in a fluid in an animal), bind with the analyte (or vice versa). As such, some, all or substantially all of the receptor molecules within a given layer may bind with the analyte, which results in a change in the optical properties of one or more of the layers.

The degree to which such binding takes place is dependent upon, among other things, the concentration of analyte in, for example, the fluid or matrix in the body of an animal. The concentration of analyte may be determined by measuring, evaluating and/or analyzing the optical response of the layer(s). That is, in one embodiment, the concentration of the analyte may be determined by optically interrogating the layer(s), determining one or more optical properties of the layer(s) (and/or the constituents thereof, and analyzing or relating the one or more optical properties of the layer(s) to an analyte concentration.

In one embodiment, the sensing device may be disposed in the animal body. The layer(s) of the device may be optically examined or interrogated via invasive or non-invasive techniques. The optical response of the layer(s) and/or, in particular, the substance within the layer(s), may be measured, evaluated and/or analyzed. The concentration of the analyte may be determined using the optical response of the layer(s) and/or the constituents or substance within the layer(s).

Figure 1A:
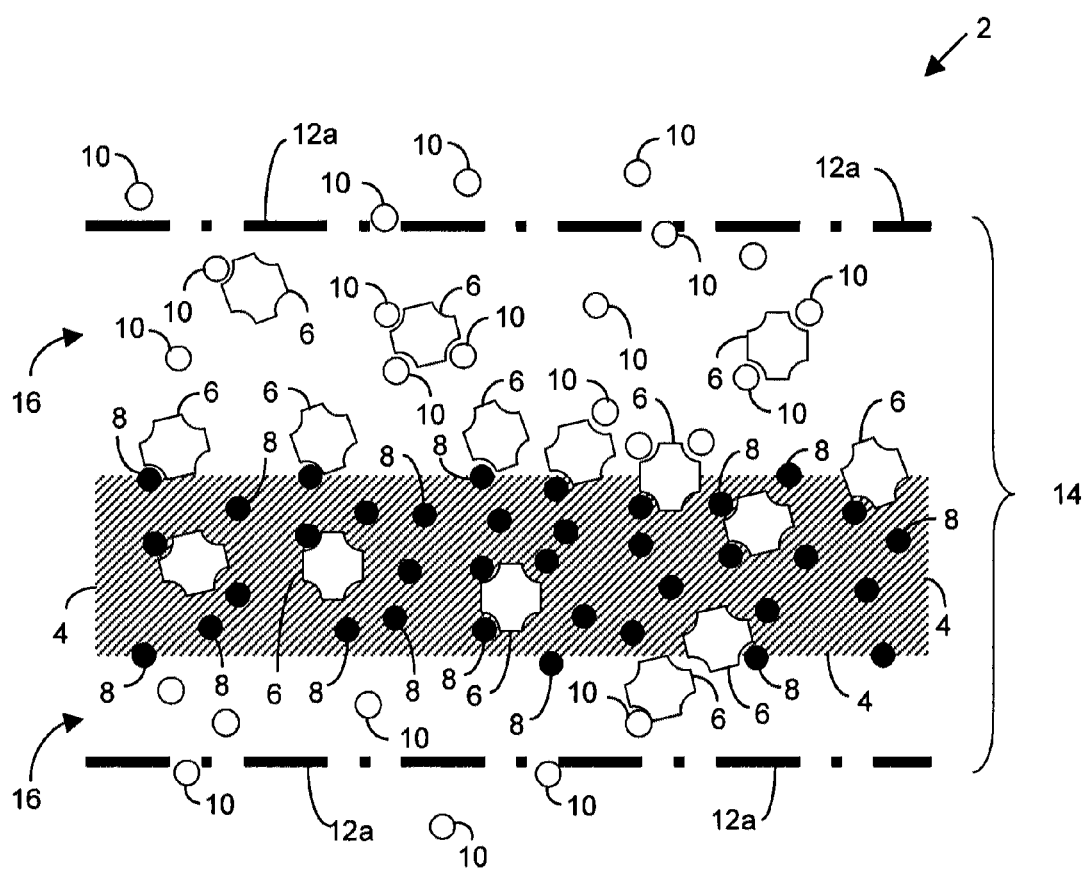
FIGS. 1A, 1B, and 1C are schematic representations of a portion of an analyte sensing device, including the turbidity sensor layer, according to one embodiment of the invention.

With reference to FIG. 1A, in one embodiment, analyte sensing device 2 includes a fluid layer or matrix layer 4 having analyte binding receptor molecules or sites 6 (hereinafter, collectively "analyte binding molecules 6"). The binding receptor molecules 6 may be bound to one or more analyte equivalent residues 8 and the combination thereof may reside within layer 4. Notably, under certain circumstances, the binding receptor molecules and/or analyte equivalent residues may migrate outside layer 4 (for example, when its binding to the analyte-equivalent residues 8 is displaced by available analyte 10 (for example, glucose)), as described in detail below.

In one embodiment, fluid or matrix layer 4 may be a hydrogel composed of, for example, one or more porous sheets or of a plurality of hydrogel beads, or a combination thereof. The predetermined analyte-binding receptor molecule 6 may be, in the case of glucose sensing, Concanavalin A ("ConA") or *Lens culinaris* lectin or other lectin or molecule. Indeed any analyte-binding receptor molecule that can reversibly bind glucose is considered to fall within the scope of the present invention. The analyte-binding receptor molecule 6 may be bound to analyte-equivalent residues 8 within matrix layer 4.

Notably, in one embodiment where matrix layer 4 is a hydrogel and analyte-binding receptor molecule 6 is a ConA, the concentration range of the mobile glucose-specific protein ConA may be substantially in the range of 3 to 30 mg per ml of hydrogel volume. Preferably, however, the glucose-specific protein ConA is substantially between 10 and 20 mg per ml of hydrogel volume.

Further, the hydrogel may have a binding capacity for the mobile binding ligand substantially ranging from 5 to 30 mg per ml of hydrogel volume. Preferably, however, the mobile binding ligand is substantially between 10 and 25 mg per ml of hydrogel volume.

Notably, in this embodiment, the invention may be used in a hydrophilic, aqueous environment. In this regard, a hydrophilic material, such as a water-swelled matrix consisting of cross linked polymers like polysaccharides, proteins, or synthetic chemicals (bis-acrylamide, etc.) may be preferred.

In those instances where a high surface area of matrix layer 4 is provided or desired for high, increased or enhanced binding capacity, the hydrogel should have a good porosity for penetration and binding of the mobile binding ligand (for example, analyte binding receptor molecules 6) inside or at the edges of matrix layer 4. As such, matrix layer 4 may consist of a continuous flat shape—and, where layer 4 is a hydrogel, it may have a thickness of substantially between 0.1 and 3 mm. Preferably, however, the thickness is substantially between 0.2 and 1 mm.

Where matrix layer 4 is comprised of beads, matrix layer 4 may be a thin, dense layer of individual hydrogel beads. Each bead may have a size of substantially between 1 and 500 microns, but preferably substantially between 10 and 40 microns.

In those instances where matrix layer 4 is comprised of a hydrogel, analyte equivalent residues 8 may be an intrinsic part of the cross linked polymer forming the hydrogel, and/or the attachment of glucose-residues to the hydrogel may be realized by chemical conjugation of respective linker molecules cross linking glucose or other suitable glucose-equivalent (for example, Dextran) with the hydrogel.

With continued reference to FIG. 1A, analyte sensing device 2 may also include a membrane or an encapsulation layer 12a (hereinafter "membrane layer 12a"). In one embodiment, membrane layer 12a is a semi-permeable matrix. Where analyte sensing device 2 is employed to measure glucose concentrations, matrix layer 4 may be comprised of a hydrogel material and the semi-permeable matrix may be permeable to glucose but not to a glucose-binding receptor molecule (more generally, analyte binding receptor molecules 6), for example, ConA.

In one embodiment, matrix layer 4 (for example, hydrogel) may be disposed or "sandwiched" between two semi-permeable membranes 12a or within a tubular construct of semi-permeable membrane, for example a hollow fiber or dialysis tubing. The membranes 12a may be comprised of, for example, regenerated cellulose acetate. The molecular weight ("MW") cut-off of each membrane 12a should be large enough for fast in- and efflux of the analyte (for example, glucose), but small enough to retain analyte binding receptor molecules 6. For example, where analyte binding receptor molecules 6 are ConA (MW=105,000), membrane 12a may have a cut-off weight substantially between, for example, 3,000 to 15,000 Da. In this way, (mobile) analyte binding receptor molecule 6 may be prevented from "leaking out" of analyte sensing device 2.

Figure 1B:
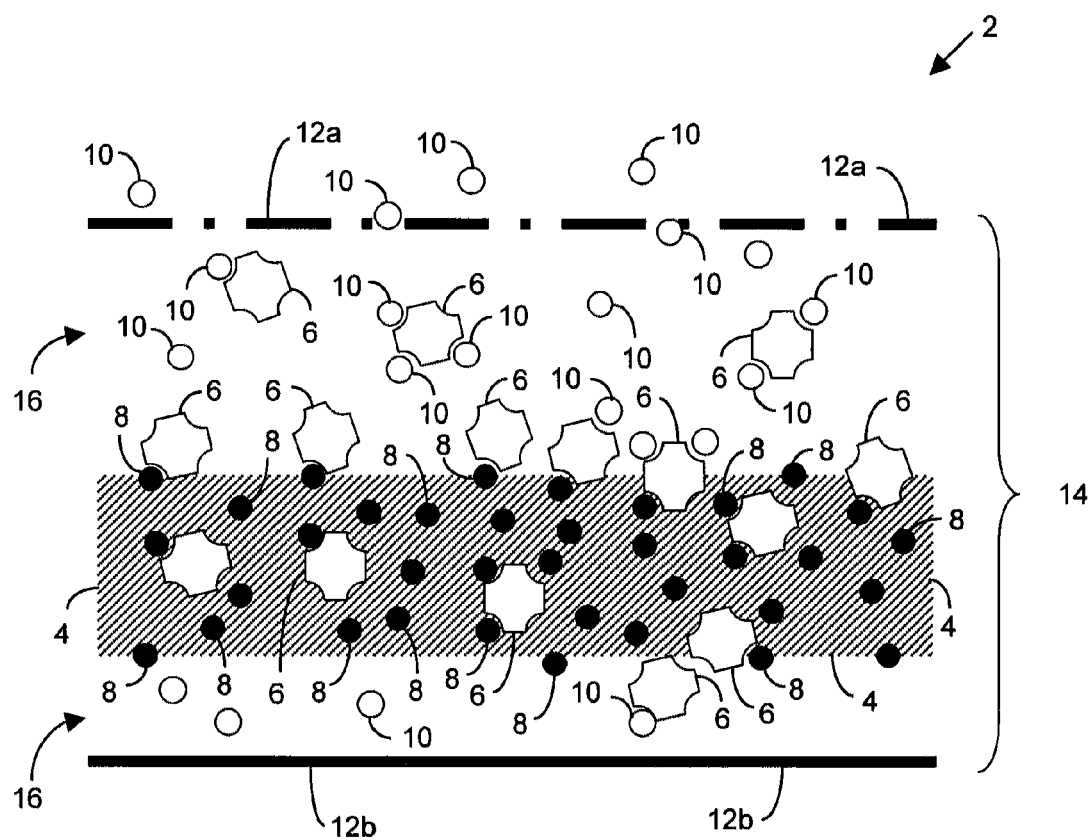
Figure 1C:
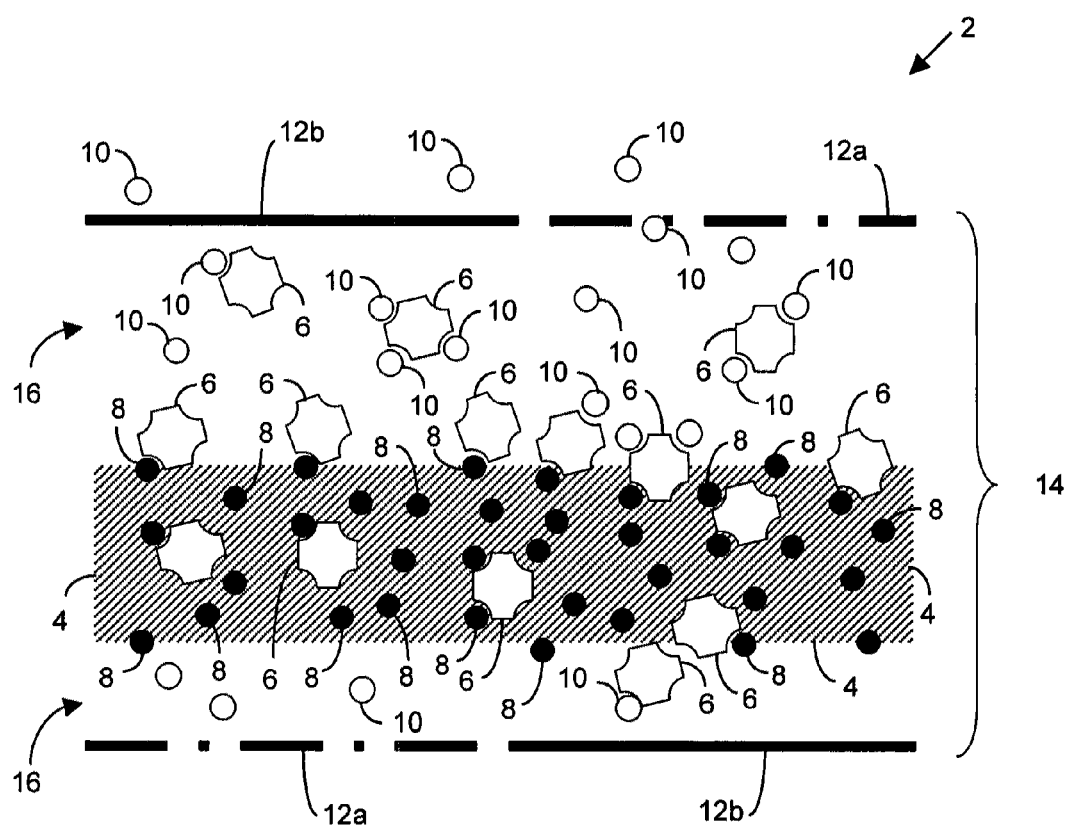

Notably, in the event that fast in- and efflux of the analyte is to occur in certain locations but not other locations, the membranes 12a may include semi-permeable portions or areas 12a to facilitate in- and efflux of the analyte and non-permeable portions or areas 12b to inhibit or prevent in- and efflux of analyte 10. (See, for example, FIGS. 1B and 1C). In this way, greater flexibility or control of the sensing process may be obtained.

In one embodiment, the hydrogel of matrix layer 4 may also be encapsulated by coating with a thin layer of polymer such as poly(ethylene glycol) (PEG), calcium alginate, acrylimide, or other suitable material whose function or purpose is the same as the cellulose membrane. The hydrogel and the encapsulating techniques are represented as a sensor layer 14. The sensor layer 14 may have an overall thickness of substantially between 0.2 and 3 mm, but preferably substantially between 0.5 and 1 mm. The sensor layer 14 may be optically transparent or semi-transparent relative to the wavelength of the radiation used to sense, sample, analyze and/or measure the concentration of analyte 10. As such, sensor layer 14 may be opaque relative to wavelengths not used to sense, sample, analyze and/or measure the analyte concentration.

In one embodiment, layer 14 includes or employs a sealing material having "leak proof" or "leak resistant" properties, such as silicone elastomer, or cyanoacrylate. This sealing material acts as a sealant of the pertinent constituents of the sensor device 2.

With continued reference to FIG. 1A, in operation, analyte 10 (for example, glucose) diffuses through membrane layer 12a allowing "equilibration" between the concentration of analyte 10 inside (or internal) and outside (or external) of sensor layer 14. In this way, "free" or unbound analytes 10 may diffuse through membrane layer 12a and bind with binding sites on analyte binding receptor molecules 6. Such analytes 10 may or may not displace analyte-equivalent residues 8 that are temporarily bound to mobile receptor molecules 6 that reside or are disposed in embedded within matrix layer 4. In the event that analyte 10 displaces analyte-equivalent residue 8, (mobile) analyte binding receptor molecules 6 may be "freed" from matrix layer 4.

The movement of mobile receptor molecules 6 into the extra-matrix space 16 may produce a measurable change in or modification of one or more of the optical properties or response of matrix layer 4. In a preferred embodiment, the change in optical properties or response includes at least a change in the optical turbidity of matrix layer 4, i.e., the degree to which electromagnetic radiation is scattered by the media comprising matrix layer 4.

In the context of glucose sensing using ConA as analyte binding receptor molecules 6, the migration of mobile receptor molecule ConA (here, analyte binding receptor molecules 6) out of matrix layer 4, which is comprised of for example Sephadex™, may cause a decrease in turbidity of matrix layer 4, sensor layer 14 and/or sensor 2 (i.e., a decrease in the degree to which the layer scatters radiation (light) incident upon it). The magnitude of this change depends on the degree of analyte binding receptor molecules 6 dissociation from matrix layer 4 and thus on the concentration of analyte (here, glucose).

Notably, the magnitude of the change in turbidity may also vary as a function of the wavelength of the incident radiation employed to interrogate or analyze the sensor layer 14. As such, a method for determining the concentration of analyte 10, then, may consist of measuring the turbidity of matrix layer 4, sensor layer 14 and/or sensor 2, and relating this measurement to the concentration of analyte 10 present in sensor 2.

The optical properties or characteristics of sensor layer 14 may be analyzed using a number of techniques. All techniques for obtaining, sensing, sampling, measuring, determining and/or acquiring one or more of the optical properties or characteristics of matrix layer 4, sensor layer 14 and/or extra-matrix space 16, whether now known or later developed, are intended to fall within the scope of the present invention.

In a preferred embodiment, the turbidity of matrix layer 4, sensor layer 14 and/or sensor 2 includes providing incident radiation to matrix layer 4, sensor layer 14 and/or sensor 2, receiving, measuring, sampling and/or sensing at least a portion of the incident radiation which has been transmitted through matrix layer 4, sensor layer 14 and/or extra-matrix space 16, and determining the turbidity of matrix layer 4, sensor layer 14 and/or sensor 2 based on the relative amount of radiation received and the attenuation of the incident radiation by matrix layer 4, sensor layer 14 and/or extra-matrix space 16.

Figure 2A:
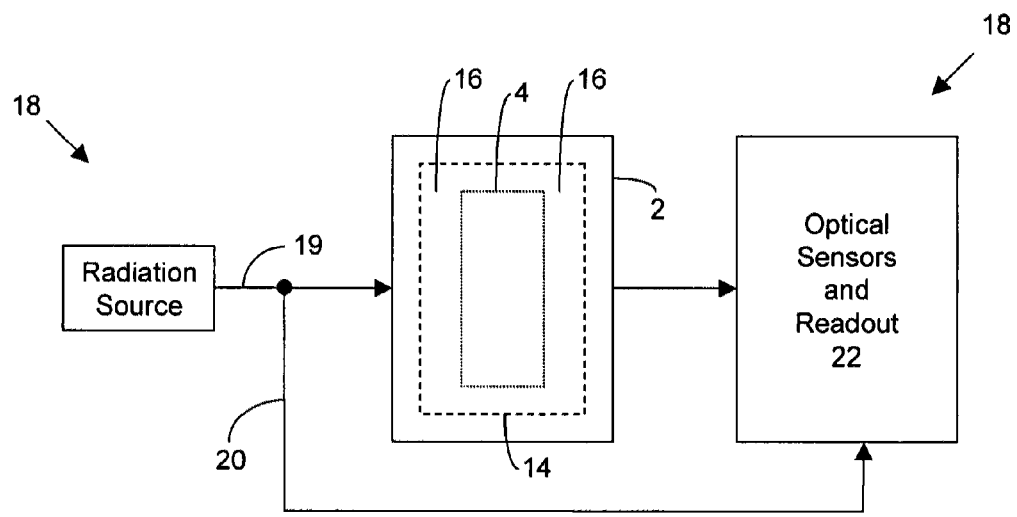
FIGS. 2A, 2B and 2C are schematic block diagram representations of exemplary systems and techniques to measure the transmission of a turbidity sensor layer of an analyte sensing device, in accordance with embodiments of the present invention. Notably, the layer with low turbidity due to, for example, high glucose (FIG. 2B) measures, senses and/or reads high transmission. The layer with high turbidity (FIG. 2C) measures, senses and/or reads low transmission.

In one embodiment, a spectrophotometer may be employed to sense, sample, measure, determine and/or acquire the optical properties or characteristics of matrix layer 4, sensor layer 14, extra-matrix space 16 and/or sensor 2. With reference to FIG. 2A, matrix layer 4, sensor layer 14 and/or extra-matrix space 16 may be placed into the optical path of sample beam 19 of a spectrophotometer 18 (further having a reference beam 20 and optical sensors and readout 22) to determine the amount of radiation transmitted through matrix layer 4, sensor layer 14 and/or extra-matrix space 16 (and, thereafter, using the amount of radiation to determine the concentration of analyte therein).

Figure 2B:
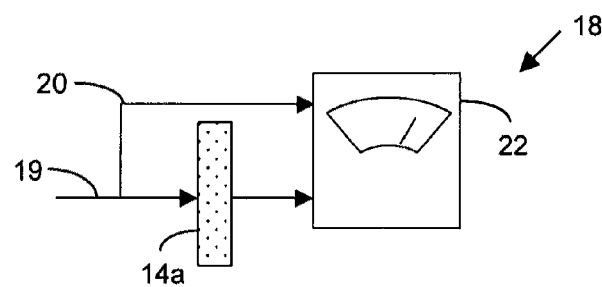

For example, with reference to FIG. 2B, measurement of turbidity in sensor layer 14a (and/or matrix layer 4 and/or sensor 2, not illustrated) having a relatively high concentration of analyte (i.e., low turbidity) will lead to an increase in the detected transmitted radiation, and therefore, this measurement may be related or correlated to the concentration of analyte (for example, glucose) in matrix layer 4, sensor layer 14 and/or extra-matrix space 16.

Figure 2C:
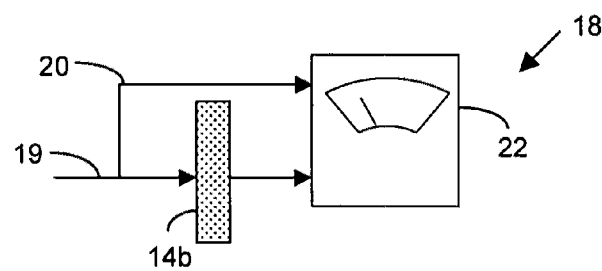

With reference to FIG. 2C, conversely, measurement of turbidity in sensor layer 14b (and/or matrix layer 4 and/or sensor 2, not illustrated) having a relatively low concentration of analyte (i.e., high turbidity) will lead to a decrease in the detected transmitted radiation.

Figure 3A:
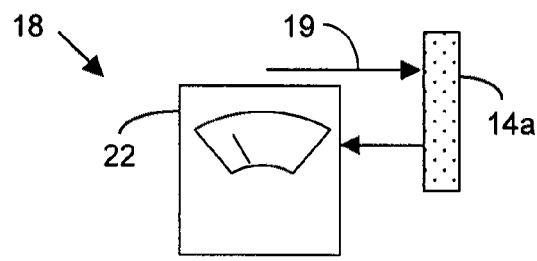
FIGS. 3A and 3B are schematic block diagram representations of exemplary systems and techniques, employing exemplary back-scatter measurement techniques of a turbidity sensor layer of an analyte sensing device, in accordance with one embodiment of the present invention. Notably, the layer with low turbidity due to, for example, high glucose (FIG. 3A) measures, senses and/or reads low back-scatter. The layer with high turbidity (FIG. 3B) measures, senses and/or reads high backscatter.
Figure 3B:
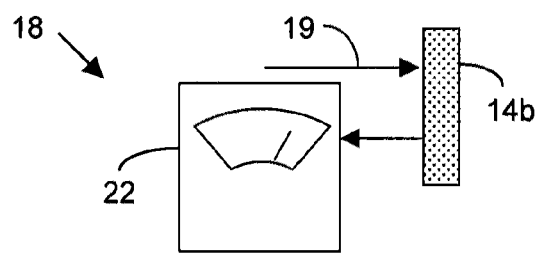
Figure 4:
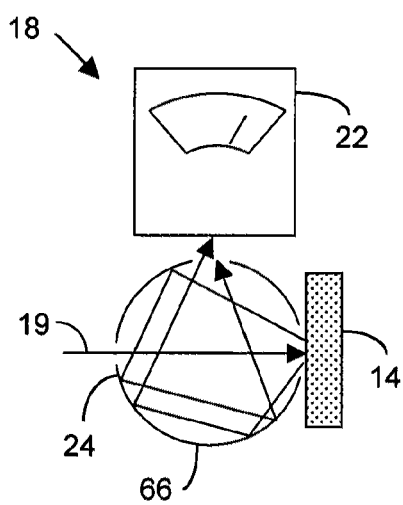
FIG. 4 is a block diagram representation of exemplary back-scatter measurement technique of a turbidity sensor layer of an analyte sensing device using an integrating sphere, in accordance with one embodiment of the present invention.

In another embodiment, with reference to FIGS. 3A and 3B, radiation may be received after any scattering "backward" as a result of matrix layer 4, sensor layer 14 and/or extra-matrix space 16. In this case, as the turbidity (due to, for example, the glucose concentration) is decreased, the amount of light that is back-scattered will decrease as well. Indeed, in one embodiment, an integrating sphere 66 may be employed to more efficiently collect the light that is backscattered by matrix layer 4, sensor layer 14 and/or extra-matrix space 16 (see, for example, FIG. 4).

Figure 5A:
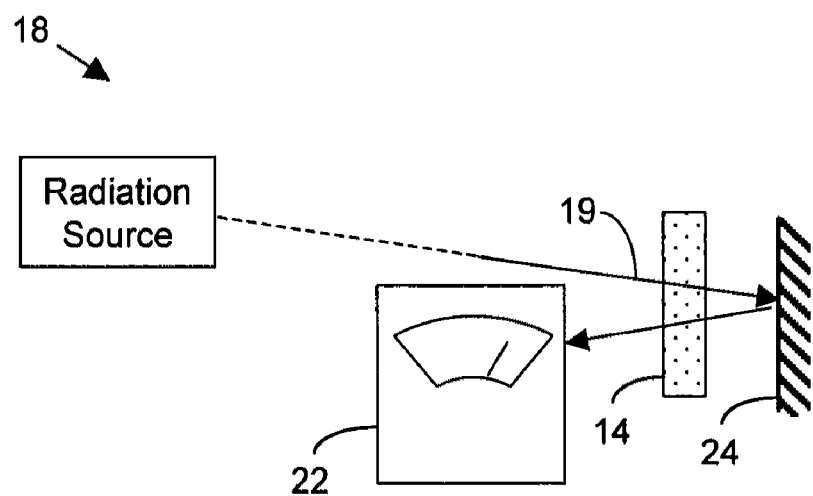
FIGS. 5A and 5B are schematic block diagram representations of exemplary systems and measurement techniques using reflection of a target through a turbidity sensor layer of an analyte sensing device, according to one embodiment of the present invention. Notably, the reflective target placed distal to layer and layer with low turbidity due to, for example, high glucose, (FIG. 5A) measures, senses and/or reads high back-reflection. The layer with high turbidity (FIG. 5B) measures, senses and/or reads low back-reflection.
Figure 5B:
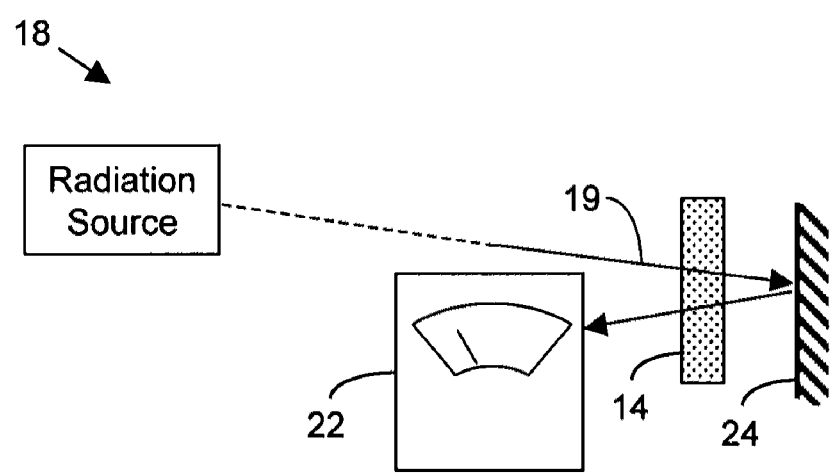

In yet another embodiment, the turbidity of matrix layer 4, sensor layer 14 and/or extra-matrix space 16 may be obtained, sensed, sampled, measured, determined and/or acquired using the apparatus and technique of FIGS. 5A and 5B. In this embodiment, matrix layer 4, sensor layer 14 and/or extra-matrix space 16 is disposed between the radiation source and reflective target 24. Thus, as the turbidity of matrix layer 4, sensor layer 14 and/or extra-matrix space 16 decreases, the amount of radiation which reaches reflective target 24 and which is transmitted back through matrix layer 4, sensor layer 14 and/or extra-matrix space 16 increases—which results in an increase in received back-reflected radiation. (See, for example, FIG. 5A). Conversely, as the turbidity of matrix layer 4, sensor layer 14 and/or extra-matrix space 16 increases, the amount of radiation which reaches reflective target 24 and which is transmitted back (therethrough) decreases. This results in a decrease in received back-reflected radiation. (See, for example, FIG. 5B).

It should be noted, however, that the orientation of the radiation source and receiver should be chosen such that interference from back-scatter or back-reflection by matrix layer 4, sensor layer 14 and/or extra-matrix space 16 is not detected in amounts which may interfere with acquisition of the desired information.

Figure 6A:
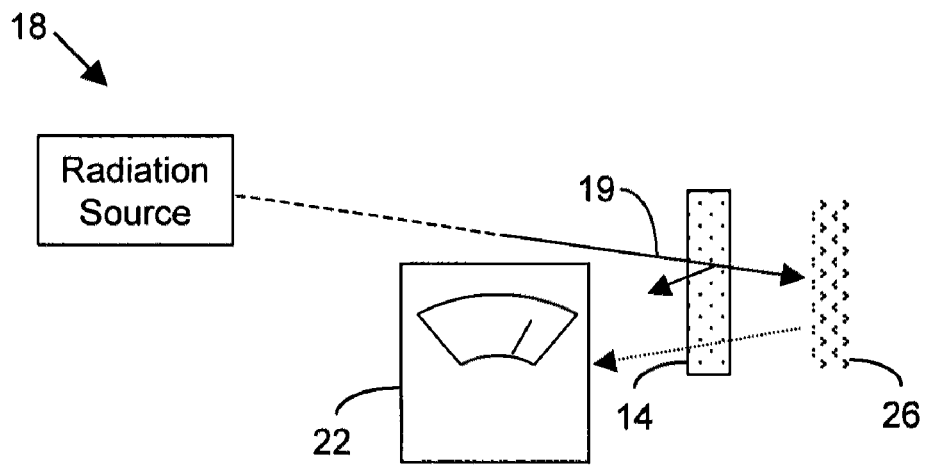
FIGS. 6A and 6B are illustrations of an exemplary measurement of fluorescence, in conjunction with an analyte sensing device, according to one embodiment of the present invention. Notably, layer with low turbidity due to, for example, high glucose, (FIG. 6A) transmits excitation light (solid arrow) and fluorescent emission light (dashed arrow) for a high fluorescence reading. The reflected light at the excitation wavelength is "rejected". The layer with high turbidity (FIG. 6B) results in a reduction in detected fluorescence.
Figure 6B:
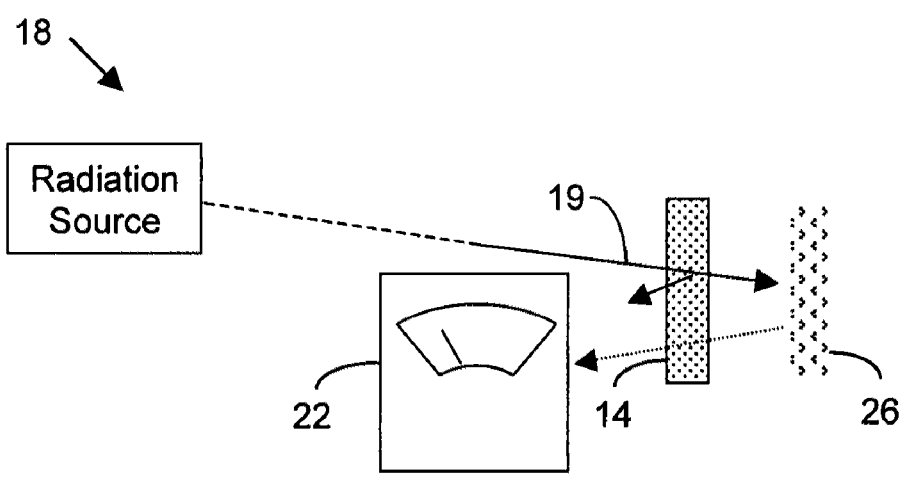

In those instances where it is desirable to increase specificity, fluorescent target 26 may be employed in conjunction with, or as a substitute for reflective target 24. With reference to FIG. 6, matrix layer 4, sensor layer 14 and/or extra-matrix space 16 is disposed between the radiation source (not illustrated) and fluorescent target 26—which when excited with light at a specific wavelength, emits light at a separate predetermined wavelength(s). In this embodiment, the fluorescent light detected by optical sensors 22 emanates from the fluorescent target, thus ensuring that attenuation of received fluorescence is due to attenuation of both excitation and emission radiation by matrix layer 4, sensor layer 14 and/or extra-matrix space 16. Notably, the detected fluorescence may increase or decrease with layer turbidity depending on the arrangement or configuration of the sensing device; as such, both cases are intended to be within the scope of the embodiment.

Notably, any fluorescent technique may be employed in conjunction with the inventions described and illustrated herein. Indeed, the present inventions may be implemented in conjunction with the FRET system and techniques described and illustrated in non-provisional patent application "Device and Method for Analyte Sensing", which was filed on Dec. 12, 2003 and assigned Ser. No. 10/735,153 (hereinafter "Analyte Sensing Patent Application"). In this regard, analyte sensing device 2, fluid layer or matrix layer 4, analyte binding receptor molecules 6, analyte equivalent residues 8, membrane or encapsulation layer 8 and sensor layer 14 may include (in addition or in lieu thereof) the sensors, systems, devices, features, attributes, alternatives, materials and/or techniques described and illustrated in Analyte Sensing Patent Application. In this way, the present invention may employ multiple optical based inspection techniques to characterize, determine, analyze and/or evaluate the concentration of analyte 10 in a fluid (for example, a fluid in or from an animal body). It is expressly noted, however, that the entire contents of the Analyte Sensing Patent Application including, for example, the devices, systems, features, attributes, alternatives, materials, techniques and advantages of all of the inventions, are incorporated by reference herein.

A spatially localized technique, for example, optical coherence tomography ("OCT") technique, may also be implemented to enhance or increase the specificity of the detected signal when obtaining, sensing, sampling, measuring, determining and/or acquiring the optical properties or characteristics (for example, turbidity) of matrix layer 4, sensor layer 14 and/or extra-matrix space 16. The principles of OCT are well known to those skilled in the art (see, for example, U.S. Pat. No. 5,321,501 and/or U.S. Pat. No. 5,459,570, which are incorporated herein by reference); and the signal related to the turbidity of a sample under study has also been described (see, for example, U.S. Pat. No. 6,725,073, Kholodnykh, et al. "Precision measurement of tissue optical properties with optical coherence tomography" Applied Optics, 42(16):3027-37, 2003, and/or Larin, et al. "Noninvasive blood glucose monitoring with optical coherence tomography", Diabetes Care, 25(12):2263-7, 2002; all of which are incorporated herein by reference).

Figure 7:
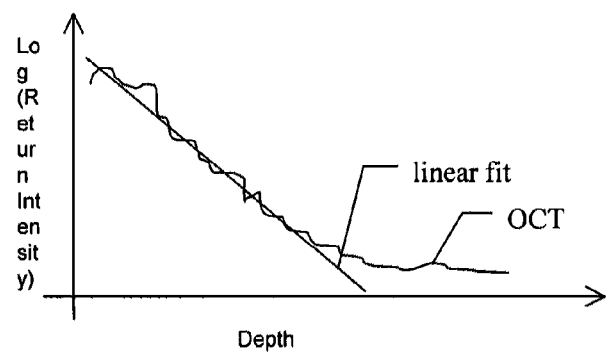
FIGS. 7 and 8 are illustrations of exemplary OCT depth scans through a turbidity sensor layer of an analyte sensing device, according to one embodiment of the present invention. Notably, (1) OCT depth scan through layer plotted as Log (Intensity) vs. Depth for return signal; the line is linear fit to scan data whose slope indicates turbidity; and (2)

Briefly, with reference to FIG. 7, when implementing OCT, the back-scatter signal as a function of depth is measured, sampled, recorded and/or obtained for a cross-section of the sample. The signal associated with a particular depth into the object depends on, for example, (1) the backscatter at the probed depth and (2) the attenuation of the signal by the intervening portion of the sample (that portion above the probed depth). FIG. 7 illustrates the depth-dependent return signal from an exemplary OCT scan through matrix layer 4, sensor layer 14, extra-matrix space 16, and/or sensor 2. In the region of sensor layer 14, the return signal may be expressed as $$I_{ret}(z) = I_0 e^{-2\mu_t z}$$

A linear fit of $\log(I_{ret}/I_0)$ vs. depth will have a slope of $-2\mu_t$, where $\mu_t$ is the effective attenuation coefficient and is given by $\mu_t = \mu_s + \mu_a$ where $\mu_s$ and $\mu_a$ are the scattering and absorption coefficients of sensor layer 14 (for example), respectively. Thus, if the absorption does not change appreciably, the slope of the OCT return signal may be proportional to the scattering coefficient (which directly relates to the turbidity of the layer).

Figure 8:
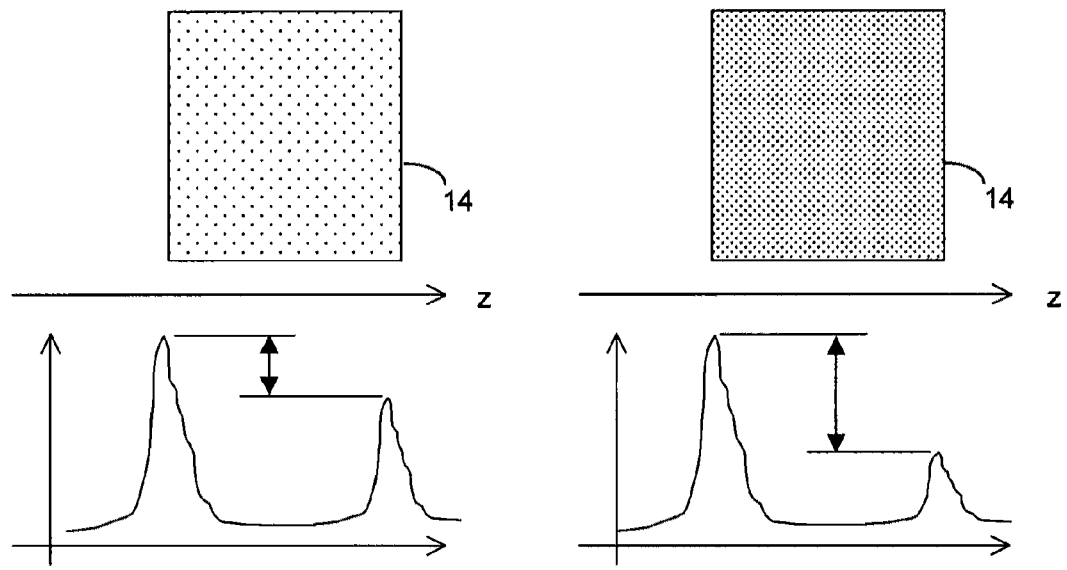

In another embodiment that employs an OCT technique, the turbidity of matrix layer 4, sensor layer 14, extra-matrix space 16 and/or sensor 2 may be measured, sampled, recorded and/or obtained by examining and/or analyzing "strong" return signals from outside matrix layer 4, sensor layer 14 and/or extra-matrix space 16. With reference to FIG. 8, two exemplary return signals from OCT depth scans through two layers of differing turbidity but having reasonably large front and back surface reflections are illustrated. By comparing the amplitudes of the front and back return signals, the attenuation due to the intervening layer may be deduced. In case of minimal or unchanged absorption, differences in this attenuation are due primarily to scattering (turbidity). Thus, the relative "heights" (amplitudes and/or phase) of the two return signals may be used to determine the turbidity and hence analyte concentration.

Notably, a desirable feature of the OCT measurement technique is that the turbidity measurements are spatially localized. This is particularly advantageous in the case where analyte sensing device 2 is implanted into tissue of an animal because the turbidity measurements are localized to the layer and relatively independent of significant changes or interference which may result from intervening tissue when employing other measuring techniques.

Figure 9:
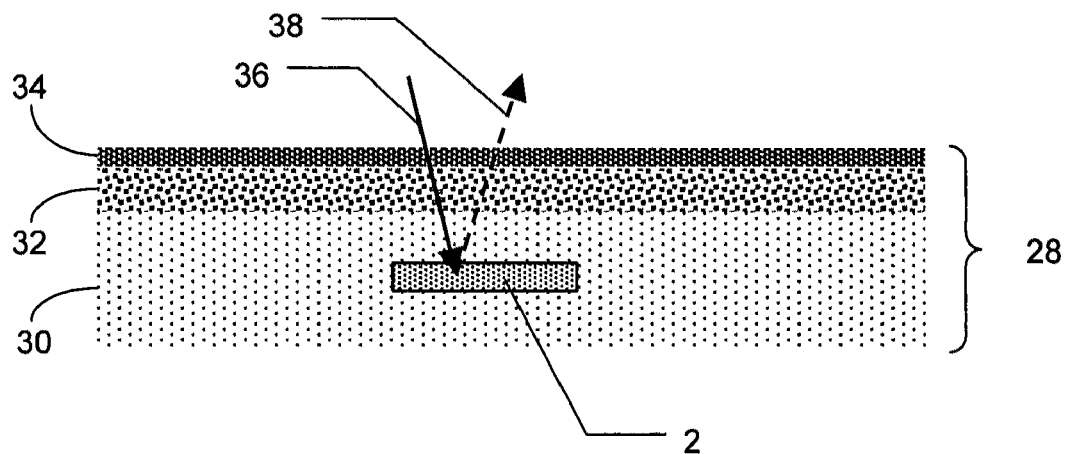
FIG. 9 is a schematic representation of a portion of an analyte sensing device, including a turbidity sensor layer that is implanted into the tissue of an animal in accordance with one embodiment of the present invention.

The analyte sensing device 2 may be disposed or implanted into tissue (for example, in the dermis of the skin) of an animal (for example, a human). In this regard, analyte sensing device 2 may be employed to measure, for example, glucose levels in a living animal. With reference to FIG. 9, sensing device 2 is implanted in skin 28. The sensor layer 14 is implanted into dermis 30 below epidermis 32 and stratum corneum 34. To optically interrogate matrix layer 4, sensor layer 14 and/or extra-matrix space 16, radiation may be delivered through the intervening layers of skin 28 along incident path 36, and radiation which is returned along return path 38, either by a corresponding layer or by a target associated with a corresponding layer, is received when it exits skin 28.

It will be appreciated that in addition to OCT, other measurement techniques capable of providing spatially localized and/or depth-resolved optical measurements may be employed including optical coherence domain reflectometry (OCDR), optical time-domain reflectometry (OTDR) or other techniques or practices known to those skilled in the art. Indeed it is intended that any technique or measurement technology capable of providing spatially localized optical measurements, whether now known or later developed, is to be included within the scope of this invention.

It should be noted that while FIG. 9 depicts analyte sensing device 2 being implanted in dermis 30, it should be recognized that, depending on the thickness of skin 28, analyte sensing device may also be implanted below dermis 30 in the subdermal (not depicted) or subcutaneous space (not depicted). Indeed, analyte sensing device 2 may be implanted in any tissue within the animal and it is particularly desirable that the tissue have two properties: in those instances where the analyte under analysis/investigation is glucose, the interstitial glucose concentration within the tissue should be closely related both temporally and fractionally to the concentration of glucose in the blood, and the device should be optically accessible (either externally or internally).

It should be further noted that in this embodiment, the turbidity, thickness, or other optically properties of the intervening tissue layers may effect or impact the return signal from matrix layer 4, sensor layer 14 and/or extra-matrix space 16. As such, it may be advantageous to implement an OCT detection technique in order to compensate, eliminate, reduce and/or minimize such effects.

Figure 10:
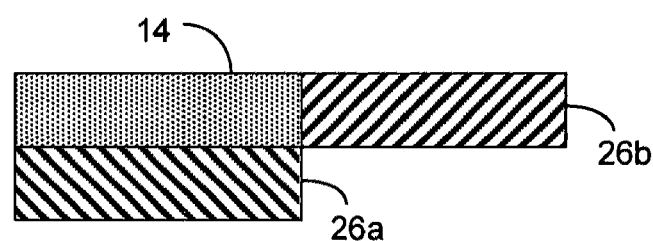
FIG. 10 is a schematic representation of a portion of an analyte sensing device, including a turbidity sensor layer having glucose-specific and glucose-independent fluorescent targets, in accordance with one embodiment of the present invention.

The impact of the effect on the return signal may also be compensated, eliminated, reduced and/or minimized by attaching to matrix layer 4, sensor layer 14 and/or extra-matrix space 16 a material or substance that is "insensitive" to the analyte of interest or under analysis/investigation and provides, produces or generates a reference signal. For example, detecting a glucose insensitive reference signal allows determination or at least compensation for the optical properties of the intervening layers and extraction of a more representative glucose sensitive signal. In this regard, with reference to FIG. 10, sensor layer 14, with glucose dependent turbidity, is disposed adjacent or near first fluorescent target 26a which provides a fluorescent return signal dependent on turbidity (and hence the concentration of glucose). A second fluorescent target 26b is not obscured by the glucose-sensitive layer 14 and thus provides a reference amount of fluorescence for a given measurement.

Preferably, fluorescent targets 26a and 26b are composed, at least partially, of fluorochromes having overlapping excitation peaks but distinct emission peaks so that their signals may be separated spectroscopically. Even more preferably, the fluorochromes should have excitation and emission peaks in the near-infrared portion of the radiation spectrum which is compatible with transmission through skin. In one embodiment, at least one pair of suitable fluorophores is Alexa647 (excitation 647 nm, emission 675 nm) and LD800 (excitation 650 nm, emission 725 nm). Alternatively, Alexa633 (excitation 633 nm, emission 660 nm), Rhodamine700 (excitation 643 nm, emission 690-785 nm), 1,1',3,3,3',3'-hexamethylindotricarbocyanine (HITC) iodide (excitation 743 nm, emission 790 nm), Oxazine750 (excitation 667 nm, emission 790-900 nm), and 1,1'-Diethyl-2,2'-dicarbocyanine iodide (DDI) (excitation 710 nm, emission 745 nm) may be employed.

Immediately below are examples of results obtained from use of certain embodiments of the present invention. The parameters of the examples are detailed therein.

EXAMPLE A

Figure 11:
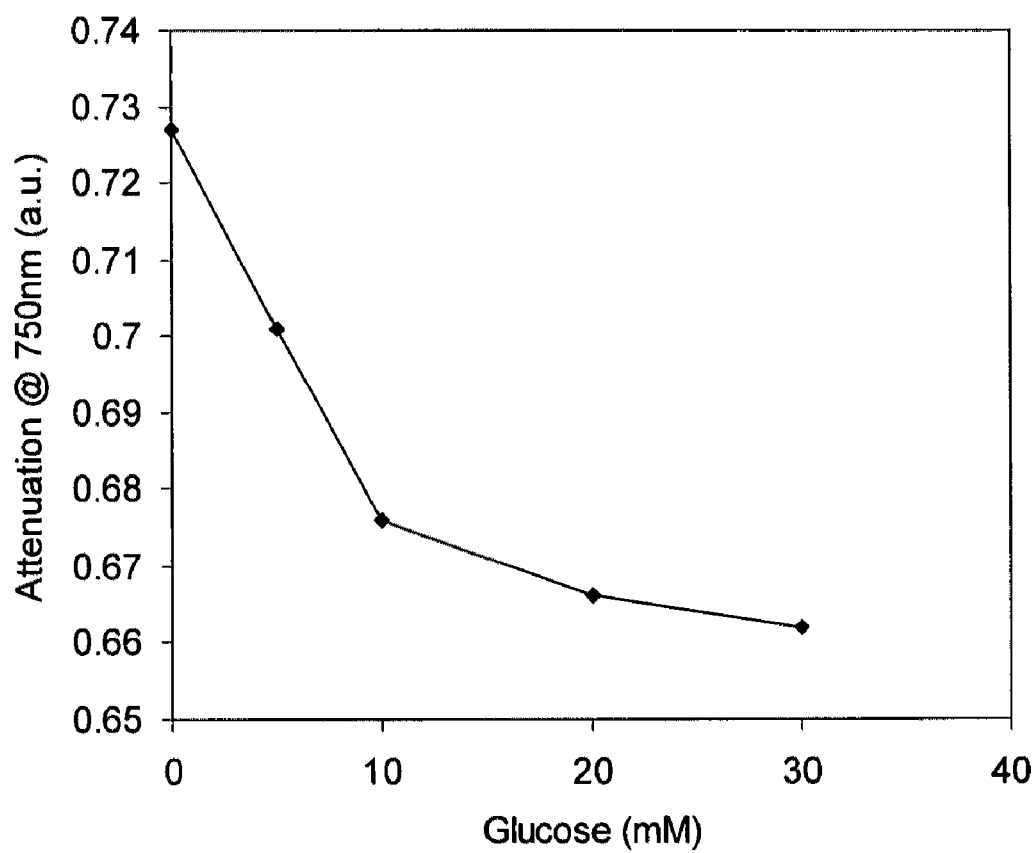
FIG. 11 is a graphical representation of optical density versus glucose concentration (see, EXAMPLE A)

Measurement of Turbidity Change of ConA/Sephadex System at Various Glucose Concentrations A swollen suspension of Sephadex G200 hydrogel beads (bead size 10 to 40 microns) was loaded with 20 mg/ml ConA. Then aliquots of the suspension were incubated with various glucose concentrations over a period of 30 min. Suspensions were then transferred into a 1 mm path length glass cuvette and the beads were allowed to settle. The turbidity of the suspension was measured at 750 nm in a spectrophotometer. FIG. 11 graphically illustrates the decrease in dispersion turbidity over the glucose range from 0 to 30 mM.

EXAMPLE B

Figure 12:
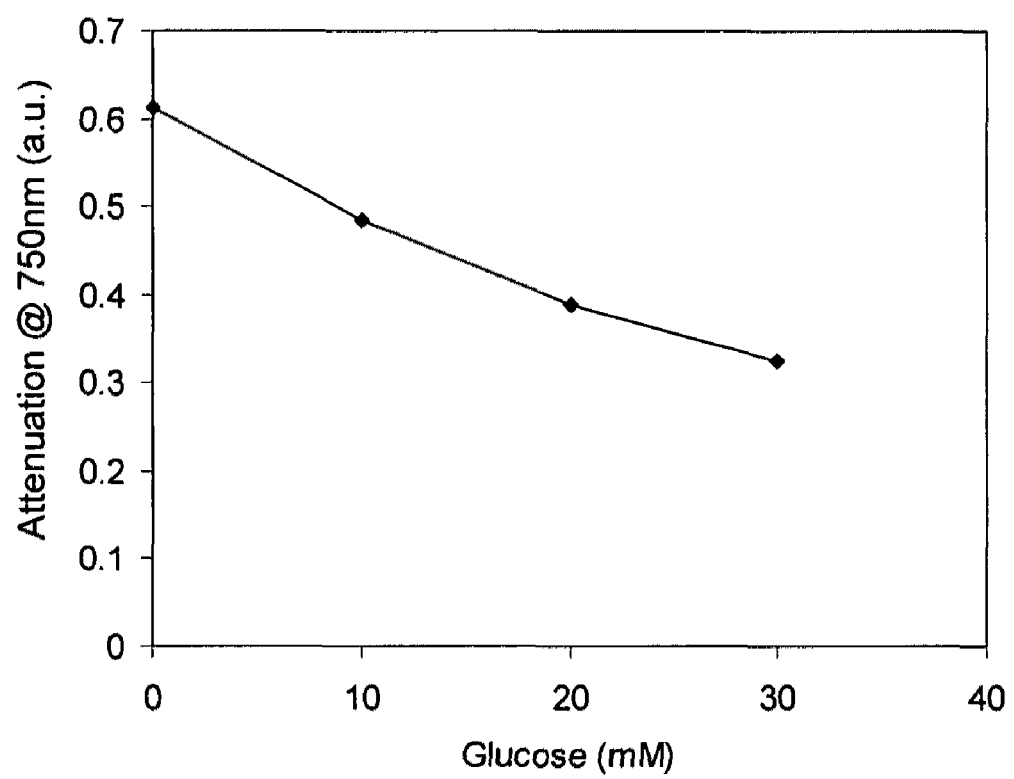
FIG. 12 is a graphical representation of optical density versus glucose concentration (see, EXAMPLE B)

Measurement of Turbidity of ConA-Sepharose/dextran "Reverse" System at Various Glucose Concentrations A swollen suspension of ConA-Sepharose hydrogel beads (bead size 60 to 135 microns) was loaded with 5 mg/ml Dextran 77,000. Thereafter aliquots of the suspension were incubated with various glucose concentrations over a period of 30 min. Suspensions were then transferred into a 1 mm path length glass cuvette and the beads were allowed to settle. The turbidity of the suspension was measured at 750 nm in a spectrophotometer. FIG. 12 graphically illustrates the decrease in dispersion turbidity over the glucose range from 0 to 30 mM.

EXAMPLE C

Reversibility of Turbidity Change in a Sensor Containing ConA/Sephadex System at Various Glucose Concentrations A wet paste of 100 µl ConA/Sephadex G200 suspension (20 mg ConA per ml hydrogel) was sandwiched inside a rectangular semipermeable dialysis capsule between two membranes made of regenerated cellulose (cutoff 10,000 Da). The thickness of the membrane capsule was approximately 0.7 mm. The dialysis capsule was sealed with cyanoacrylate adhesive. The capsule was then fixed inside a 4 ml plastic cuvette that contained saline phosphate buffer without glucose.

Figure 13:
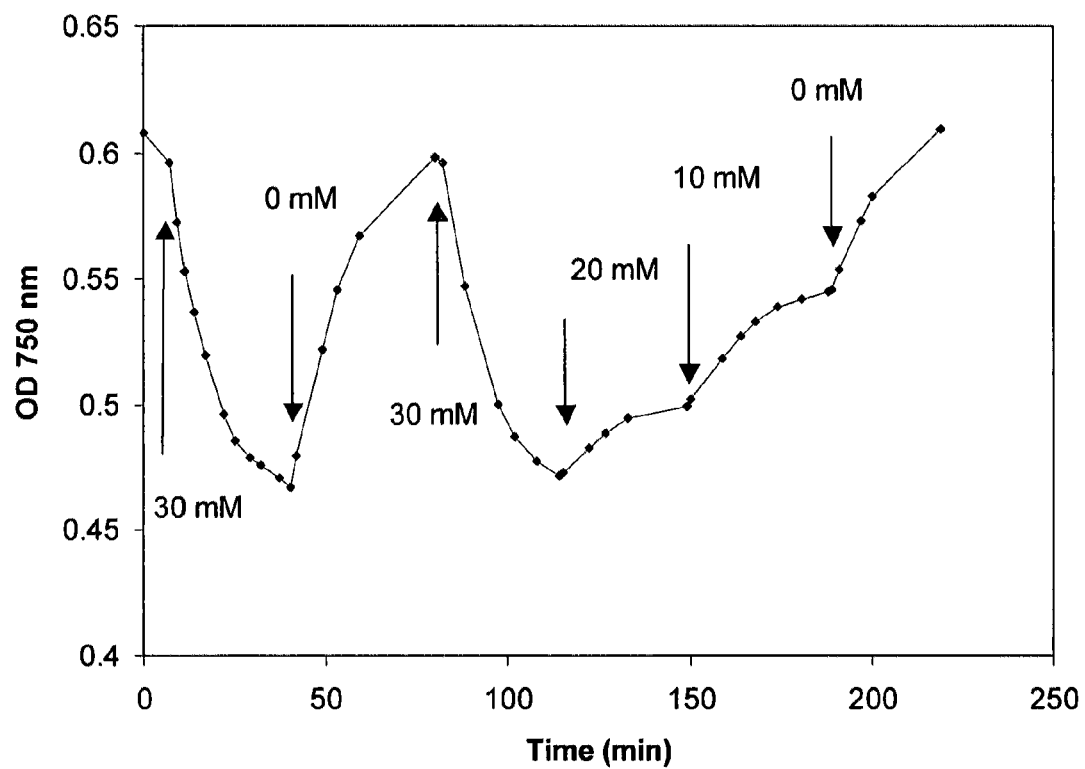
FIG. 13 is a graphical representation of optical density (turbidity) of a turbidity sensor layer as a function of time with placement in solutions of various extra-layer glucose concentrations (see, EXAMPLE C)

The cuvette was placed inside the spectrophotometer in such a way that the light beam passed through the hydrogel. Then the solution was exchanged with 30 mM glucose and the turbidity change was dynamically monitored over time. FIG. 13 shows the turbidity response of the sensor after various exchanges of glucose concentration. The turbidity change was reproducible after repeatedly switching from 30 mM to 0 mM glucose back to 30 mM. A sequential decrease of the glucose concentration from 30 to 0 mM glucose via 20 mM and 10 mM resulted in an incremental increase of the turbidity. The time response was in the order of 10 to 30 min.

EXAMPLE D

Measurement of Reversible Fluorescence Change Due to Turbidity Changes in ConA/Sephadex System at Various Glucose Concentrations In EXAMPLE D, the same sensor as in EXAMPLE C was used to measure the fluorescence change. On the back of the cuvette containing the dialysis capsule, a thin polysulphone film with encapsulated fluorescent dye LD800 (ex. 650 nm, em. 750 nm) was mounted. The sensor 2 was interrogated with light coming from a laser diode (635 nm) that was guided through a bifurcated fiber optic bundle.

Figure 14:
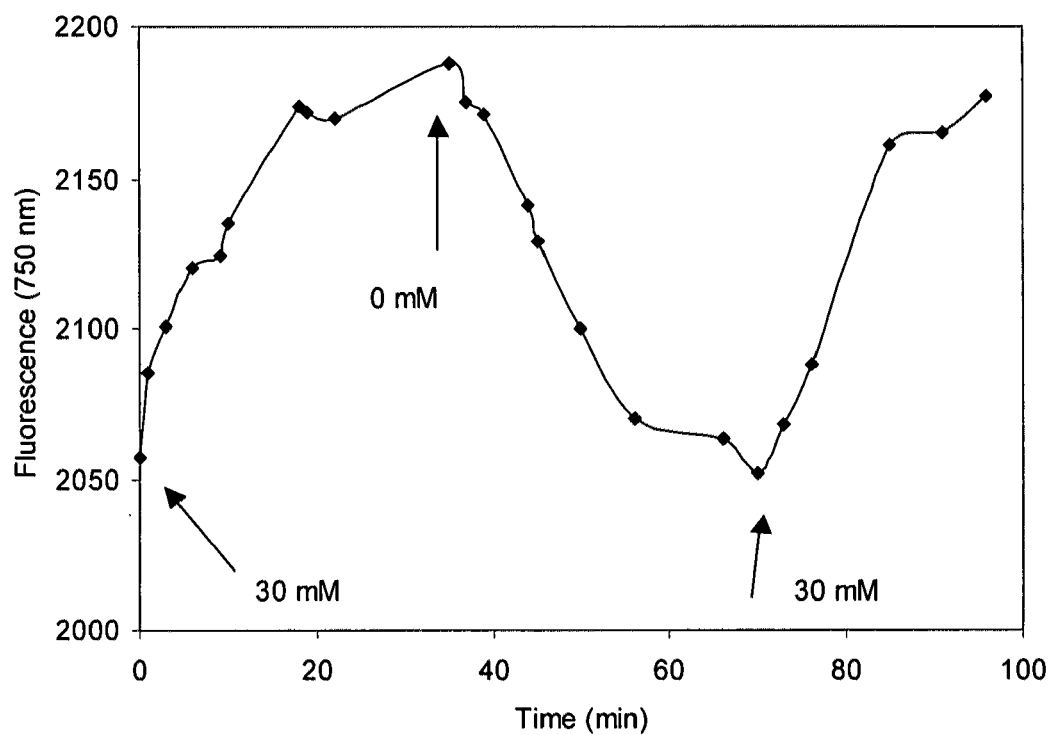
FIG. 14 is a graphical representation of fluorescence of a target appended to a turbidity sensor layer as a function of time with placement in solutions of various extra-layer glucose concentrations (see, EXAMPLE D)

The light beam coming out of the distal end of the fiber bundle passed through the hydrogel and emitted fluorescence traveling back through the hydrogel was captured with the same fiber optic bundle and directed to a fluorescence spectrometer where it was measured. While the concentration of glucose in the buffered saline solution was alternately switched from 30 mM glucose to 0 mM and back to 30 mM, the fluorescence was monitored. FIG. 14 graphically illustrates that the fluorescence increases at increasing glucose concentrations. This is expected since the turbidity decreases. The glucose induced fluorescence response was reversible and reproducible.

The present invention is applicable in the field of affinity binding assays and sensors, and covers a wide palette of life-science research and products. The present invention is a system, a device and a method for sensing the concentration of an analyte in a fluid (for example, a fluid sample) or matrix. The analyte may be glucose or any other analyte of interest. The fluid or matrix may be, for example, the fluid or matrix in the body of an animal, or any other suitable fluid or matrix in which it is desired to know the concentration of an analyte.

For example, monitoring blood glucose with a glucose-specific affinity sensor based on glucose-specific lectins is a significant application that is useful in treating diabetes. Another field of application is immunodiagnostics and immunosensors, employing the affinity binding interaction of immunoglobulins and antigens for the detections of molecules in biological fluid samples, like hormones, peptides, and proteins. In addition, the present invention may be applicable for the analytical analysis of glyco-conjugates in pharmacy and food industry by, for example, sugar detection by means of lectins. The present invention is suitable in many applications, including those in life-science research, products and techniques.

There are many inventions described and illustrated herein. While certain embodiments, features, attributes and advantages of the present inventions have been described and illustrated, it should be understood that many other, as well as different and/or similar embodiments, features, materials, attributes, structures and advantages of the present inventions, are apparent from the description, illustration and claims. As such, the embodiments, features, materials, attributes, structures and advantages of the present inventions described and illustrated herein are not exhaustive and it should be understood that such other, similar, as well as different, embodiments, features, materials, attributes, structures and advantages of the present inventions are within the scope of the present invention.

For example, the chemical configuration of the ligand-receptor system may be as follows: analyte-analogue may be immobile relative to matrix layer with receptor molecule being mobile; alternatively, receptor molecule may be immobile relative to the matrix layer and macromolecular analyte-analogue being mobile. The alternative assay may be realized by preparing a hydrophilic hydrogel matrix with receptor molecules which are covalently bound to the matrix.

Figure 15:
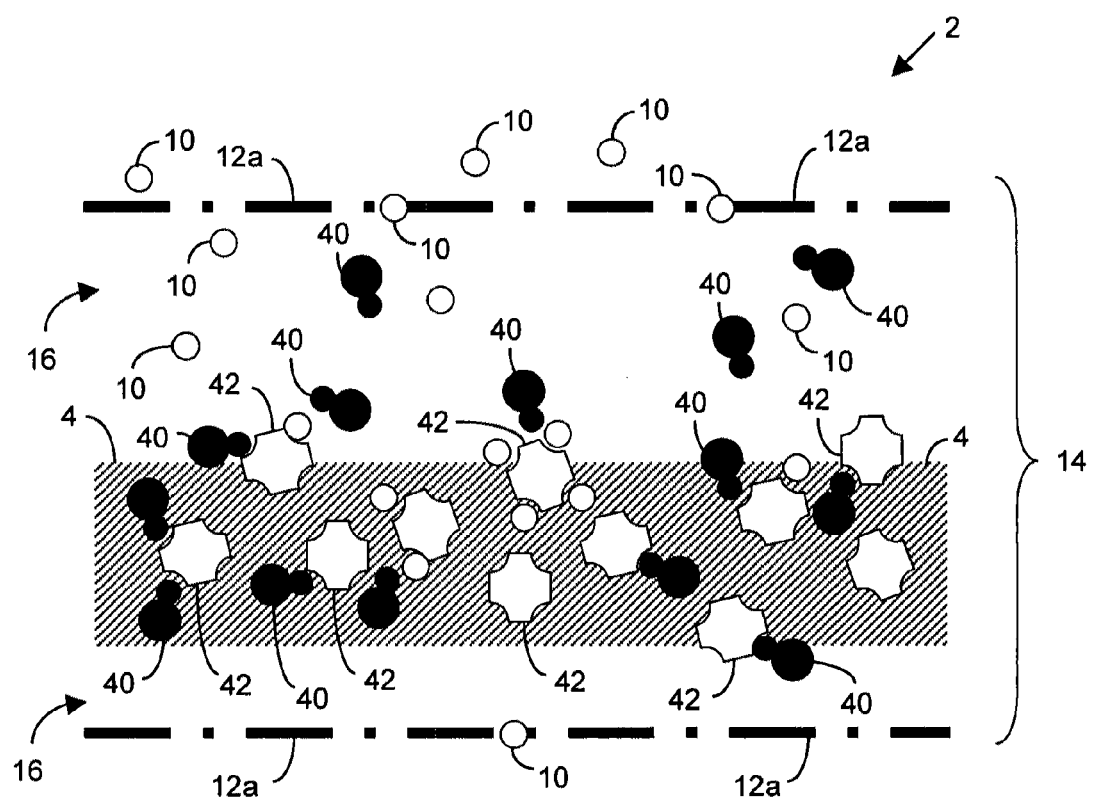
FIG. 15 is a schematic representation of a portion of an analyte sensing device, including a "reverse" assay turbidity sensor layer, according to an embodiment of the present invention.

With reference to FIG. 15, this material may then be preloaded with a macromolecular analyte-analogue 40, which is bound to the receptor molecule. When analyte 4 is introduced into the layer 14, it displaces that analyte-analogue 40 from the covalently immobilized receptor molecule 42, and analyte analogue 40 diffuses into the extra-layer or extra-matrix space 16. Since macromolecular analyte-analogue 40 is a "large" molecule, the overall turbidity of the layer decreases. The analyte-equivalent analogue may be any suitable molecule, preferably having a high molecular weight, for example, 10,000-500,000 Da. In the case where analyte sensor device 2 is employed to sense glucose concentration, the analyte-analogue may be, for example, a Dextran (e.g. 70,000 MW Dextran) or a glycated albumin (MW approximately 100,000 Da). Other molecules are suitable as well.

Further, the present invention may be formatted into a disposable sensor device having a disposable assay or a "continuous" usage—reversible sensor device. In those instances where the sensor device may be re-used, it may be advantageous to dispose sensor device 2 in a housing that allows analyte diffusion while inhibiting (or substantially inhibiting) macromolecules (receptor and/or analyte-equivalent molecule) from escaping. Such a housing may be constructed as previously mentioned by "sandwiching" the layer matrix material between two semi-permeable membranes. The layer matrix may also be coated with a semi-permeable hydrogel or equivalent material, for example, poly(ethylene glycol) (PEG). The layer matrix may also be placed inside of a semi-permeable structure such as a hollow dialysis fiber or other capsular structure, or other types of housing as suitable. As such, all techniques that permit analyte diffusion while inhibiting (or substantially inhibiting) macromolecules (receptor and/or analyte-equivalent molecule) from escaping, whether now known or later developed, are intended to be within the scope of the present invention.

In addition, matrix layer 14 may consist of material(s) that is/are compatible with the physicochemical nature of the analyte of interest. Indeed, it may be advantageous to employ or implement a hydrophilic, aqueous environment, or a hydrophilic material, such as a water-swelled matrix consisting of cross linked polymers (for example, polysaccharides, proteins, or synthetic chemicals such as bis-acrylamide). To provide a high or large surface area of the hydrogel for high binding capacity, the gel may have a high degree of porosity for penetration and binding of the mobile binding ligand inside the gel. As such, as mentioned above, the matrix layer may be, for example, a continuous flat shape with a thickness between 0.1 and 3 mm (preferably between 0.2 and 1 mm) or a thin, dense layer of individual hydrogel beads having a diameter of between 1 and 500 microns (preferably 10 to 40 microns).

Further, the choice of the receptor molecule may be dependent on the application. For glucose monitoring in the sensor format of the present invention, glucose-specific lectins may be employed—for example, ConA, and lectins from *Vicia faba, Lens culinaris*, and *Pisum sativum*.

Notably, while the discussion of the present invention has been in the context of a sensor layer or sensor layers which may be implanted wholly within the body of the animal and interrogated via external means, the present invention may also be embodied in an indwelling configuration. For example, with reference to FIG. 16, in one embodiment, the analyte sensing device 2 may be implemented in a fiber optic turbidity sensor 44. In this regard, at a distal end of fiber 46 of fiber optic turbidity sensor 44, a cylindrical plug 48 and a cylindrical semipermeable membrane 50 form an enclosed space which may be at least partially filled with analyte-sensitive matrix and molecules (medium) 52. The surface of cylindrical plug 48 may be, for example, reflective, absorptive, or scattering to radiation that is incident upon it. The incident radiation 54 is reflected, scattered and/or otherwise transmitted by medium in accordance with the analyte-sensitive optical properties of the medium 52. At least a portion of incident radiation 54 is "returned" into fiber optic turbidity sensor 44 as "received" radiation 56. The relative amount of received radiation 56 depends, to some extent, on the relative amount of incident radiation 52, the configuration of device 44, and the analyte-dependent optical properties of medium 52. Thus, also within the scope of the present invention is a technique for determining analyte concentration based on detection of the received radiation.

Figure 16:
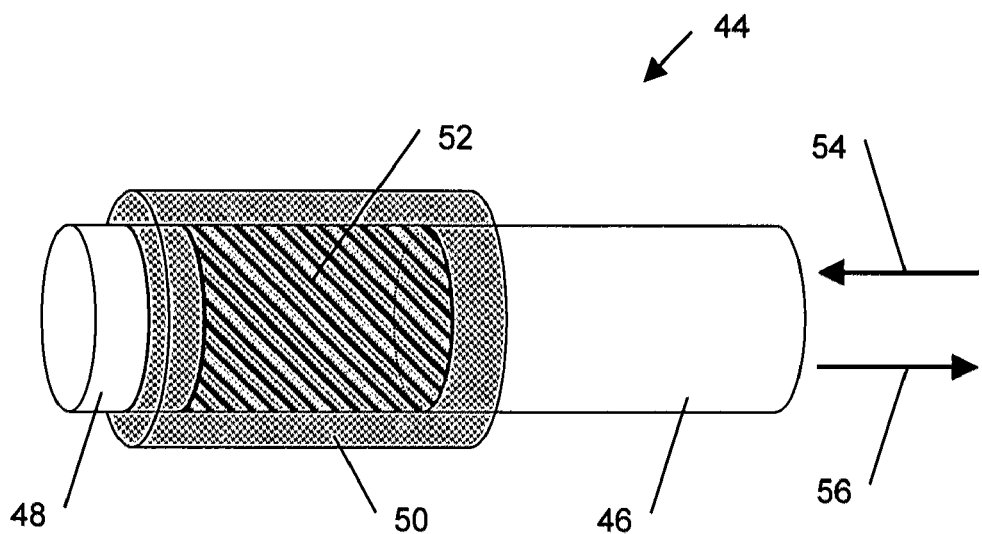
FIG. 16 is a schematic representation of a portion of an analyte sensing device, including a turbidity sensor layer disposed at a distal end of a fiber optic, in accordance with one embodiment of the present invention.

It should be noted that while FIG. 16 illustrates a single fiber optic, it may be advantageous to employ one or a plurality of fiber optics for transmission of incident radiation 54, received radiation 56, or both. It will be appreciated that plug 48 may also embody a fluorescent target (as described above) having a detected fluorescence that depends at least partially on the analyte-dependent optical properties of medium 52, and hence analyte concentration.

Figure 17:
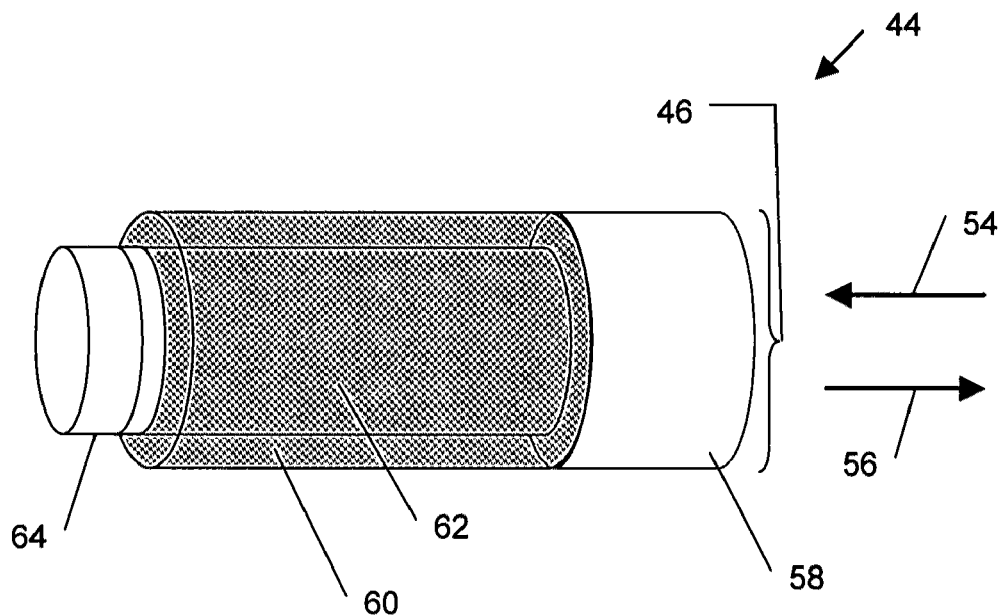
FIG. 17 is a schematic representation of an analyte sensing device, including an optical fiber having an analyte-sensitive medium as "cladding", in accordance with an embodiment of the present invention.

With reference to FIG. 17, in another embodiment, fiber optic sensor 44 includes a cylindrical shell of analyte sensitive medium 60 (and, optionally, a surrounding semi-permeable membrane) in lieu of or in addition to the distal portion of cladding 58 of fiber 46. In this embodiment, incident radiation 54 and received radiation 56 are transmitted within core 62 of fiber 46.

Notably, however, as is known to those skilled in the art, the amount or degree of transmission depends on the optical properties of core 62 and cladding 58 of fiber 46. As the optical properties of medium 60 (which acts as a cladding for core 62) change as a result of the presence of analyte, the transmission of incident radiation 54 and received radiation 56 change. Therefore, a method for determining the concentration of the analyte may depend to some extent on detecting the relative amount of received radiation 56 and relating this to one or more optical properties of medium 60 and hence to analyte concentration.

It should be further noted that an end piece 64 may be placed at the furthest end of fiber 46. The end may be made to be reflective, absorptive, and/or scattering to incident radiation. Further, end piece 64 may encompass a fluorescent target to be illuminated by incident radiation and to emit fluorescent radiation that may be received and sensed by optical fiber 46.

It will be appreciated that a change in turbidity of sensor layer 14 may be due or attributed to a number of microscopic and micro-molecular physical interactions which result in observable changes in bulk properties of the sample. As such, it will be further appreciated that the term "turbidity change" used herein may refer to a number of related or independent changes in sample optical properties or characteristics. There are a number of parameters of the sample which may be measured, sampled, recorded, detected and/or obtained. Thus, the word "turbidity" is not meant to be limiting to a specific optical property or characteristic.

For example, the scattering cross section of particles of one medium dispersed in a second medium is dependent on, among other things, the refractive indices of the two media. Therefore, the observable change in turbidity may be related to some extent to a change in refractive index of all or a part of the layer. Thus alternate techniques and systems of determining analyte concentration based on determining alternate properties of the sample based on the provided and received radiation are intended to be within the scope of the present invention.

In addition to refractive index, the absorptive properties of the layer may also change depending on the binding and positional status of mobile or immobile receptor molecules and mobile or immobile analyte-equivalent molecules, and in this case the term "turbidity" may mean "attenuation." However, as the degree of this additional attenuation of radiation is dependent on the specific layer configuration and the measurement modality employed, the "turbidity" of the layer changes. It is intended that the scope of the present invention include measurements of such additional attenuation (positive or negative) either as part of, in lieu of, or in addition to measured "turbidity."

Figure 18:
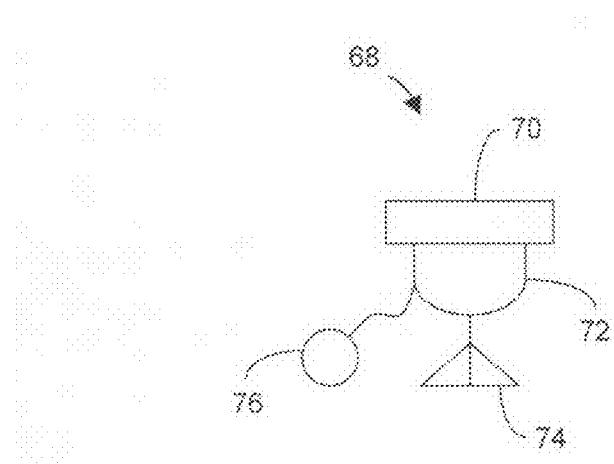
FIG. 18 is a schematic representation of a telemetry-based analyte sensing device designed to work without external radiation sources, according to an embodiment of the present invention.

In those embodiments where the analyte sensing device is disposed in portion of an animal body that is difficult to examine, detect, sample, measure and/or interrogate the optical response of matrix layer 4, sensor layer 14 and/or extra-matrix space 16 using an external radiation source and/or external sensing circuitry, it may be advantageous to include sensing circuitry/optics (and, in certain embodiments, a wireless transmitting circuitry) near or in sensing proximity to sensor 2 in order to facilitate acquiring such optical response. For example, with reference FIG. 18, in one embodiment implantable telemetry-based sensor 68 may be implanted and reside in the animal body (using well known techniques) in a portion of an animal body that permits optical "access" to sensor 2. The telemetry-based sensor 68 includes sensor layer 70, optical measurement system and telemetry electronics 72, antenna 74 and power source 76. In this embodiment, measurements taken from sensor 68 are transmitted to a receiver (not shown) outside the body without requiring external radiation sources or external circuitry.

Figure 19:
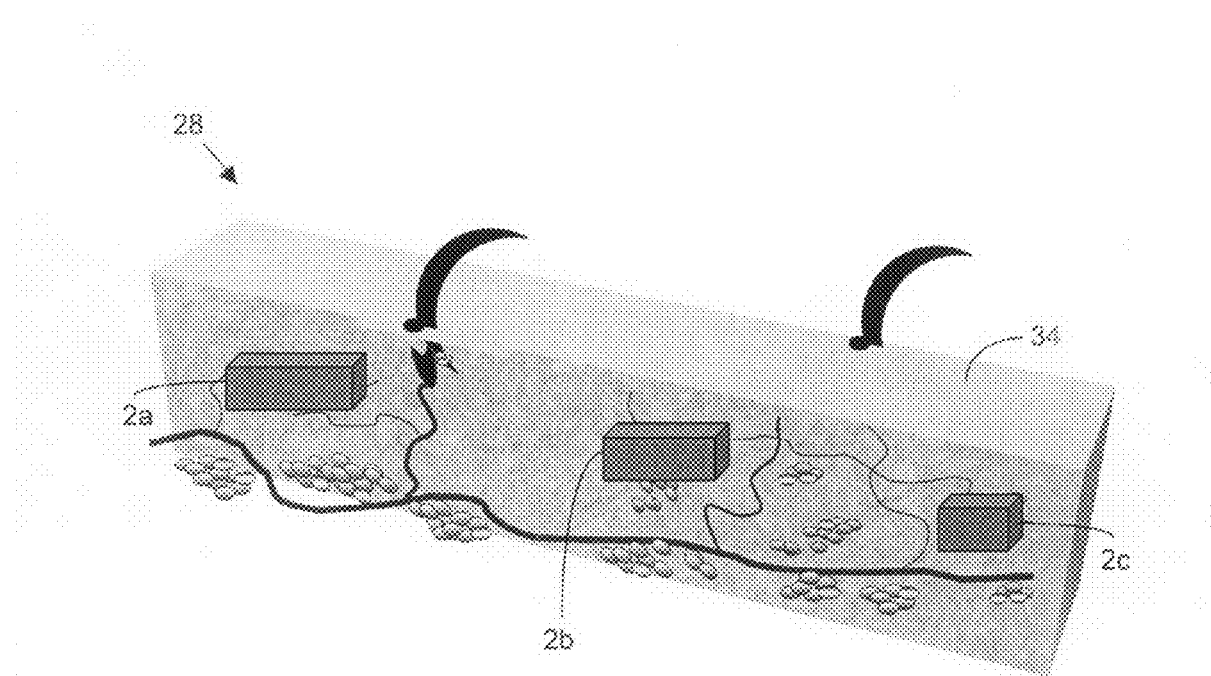
FIG. 19 is a three-dimensional cross-sectional illustration of a plurality of schematically represented analyte sensing devices, embedded in an animal body, according to one embodiment of the present invention.

It may also be desirable to simultaneously or sequentially employ a plurality of analyte sensing devices 2a-c having the same or different analyte sensitivities. (See, for example, FIG. 19). For example, the sensitivity of the analyte sensing component to the desired analyte may be adjusted by, for example, altering the ratio of analyte binding receptor molecules 6 to analyte equivalent residues 8 present in analyte sensing device 2. Such alterations may lead to sensor configurations which have predetermined and/or optimized sensitivity over prescribed regions of analyte concentration.

Alternatively, analyte sensing device(s) 2 may include a plurality of matrix layers 4, each having a predetermined and/or optimized "response" and/or interaction over prescribed regions of analyte concentration. Indeed, matrix layer 2 may include different constituents or materials such that the optical response and/or interaction with analyte binding receptor molecules 6, analyte equivalent residues 8 and/or analyte 10 changes based on concentration of analyte 10 in the fluid (for example, the fluid in or from an animal).

For example, a first analyte sensing device may be designed to be highly sensitive at low analyte concentrations, but its signal saturates at higher analyte concentrations. A second analyte sensing device, however, may be relatively insensitive at lower analyte concentrations, but may have a much larger dynamic range before saturation. Thus, these two complementary sensor formulations may be used in conjunction to accurately cover a larger range of analyte concentration values. The two devices may be discrete or may be formulated into a single, integrated sensing device.

While the use of two (or more) radiation converting chromophores has been described in detail to address and/or compensate for variations in intervening skin optics, other, more sophisticated methods of analysis may be applied to extract the radiation converting efficiency of the first radiation converting chromophore (and hence glucose concentration). For example, it may be the case that the skin or surrounding tissues contain radiation converting chromophores which would convert radiation provided by the radiation providing unit into radiation which would "overlap" with at least a portion of the provided radiation, thereby creating interference. In this situation, it may be advantageous to employ a device and technique to discern, discriminate and/or reject that portion of the detected radiation not due to analyte sensing device 10. In this regard, a number of methods for performing such rejection are known to those skilled in the art, and it is contemplated that the use, development, and/or refinement of such methods is within the scope of the present invention. Such methods may include, for example, measurement of the conversion of radiation by skin or tissue alone, normalization of this conversion efficiency by some known quantity (for example, the intensity of radiation exiting the radiation providing means), further normalization of the detected converted radiation from both skin and first and second radiation converting chromophores together, and subsequent subtraction of the radiation converted by the skin. Other methods including multivariate regression analysis or principal component analysis may also be implemented to discern, discriminate and/or reject that portion of the detected radiation not due to analyte sensing device 10 (i.e., "isolate" contribution(s) from analyte sensing device 10).

Figure 20A:
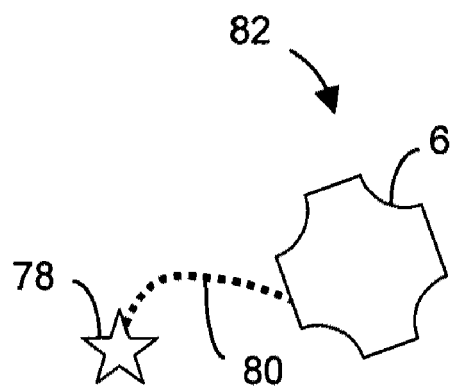
FIG. 20 is a schematic representation of analyte sensing device components designed to have increase response level due to attachment of nanoparticles.
Figure 20B:
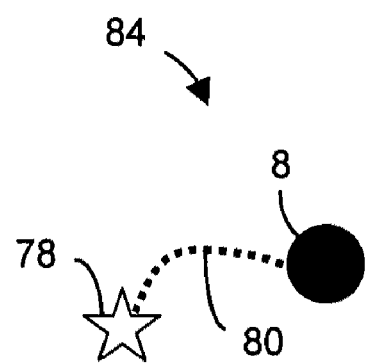

Notably, it may be advantageous to increase the sensitivity of sensor 2 by employing techniques, circuitry and/or optical components to increase the change in refractive index of one, some or all of the constituent particle(s) or matrix (matrices) of sensor 2. In this regard, in some embodiments of the present invention, it may be the case that the observed change in the turbidity or scattering coefficient of the analyte sensor layer is due (at least in part) to a bulk change in refractive index of the constituent particle(s) or matrix (matrices) of the sensor. In one embodiment, an increase in the detected or observable change in turbidity or scattering coefficient may be effected by attaching small "nano particles" to one or more of the analyte sensor components. For example, one or more nanoparticles 78 may be attached to the analyte binding receptor molecule 6 according to the schematic of a nanoparticle-conjugated analyte binding receptor molecule 82 illustrated in FIG. 20A. Alternatively, one or more nanoparticles 78 may be attached to the analyte equivalent residue 8 according to the schematic of a nanoparticle-conjugated analyte equivalent molecule 84 illustrated in FIG. 20B. Such particles may be attached directly or through an optional linker molecule 80 as shown.

In a preferred embodiment, the nanoparticles 78 can be made of various materials, such as gold, silver, selenium, or polystryrene. For example, ConA molecules with nano-particles of gold may be obtained from Nanoprobes, Inc. (Yaphank, N.Y.), and the combined nanoparticle conjugated analyte binding receptor molecule 82 may be directly substituted for analyte binding receptor molecule 6. A plurality of nanoparticles and/or materials may be used separately or combined to create nanoparticle-conjugated analyte binding receptor molecules 82 or nanoparticle-conjugated analyte equivalent 84. The size of the nanoparticles 78 ranges from 0.5 to 200 nm with the preferred size range covering 2 to 100 nm. The shape of the nanoparticles 78 can be round, oblong, rod-like, square, rectangular or other. The nanoparticles 78 may be hollow or solid or be designed to have either a smooth or rough surface. The nanoparticles 78 might be attached to the analyte binding receptor 6 or analyte equivalent residues 8 with common chemical bonds or linker molecules 80. A preferred linker molecule 80 of nanoparticles 78 to the analyte binding receptor 6 or analyte eqivalent residue 8 is sulfo-N-hydroxy-succinimido-linker which chemically reacts with primary amino-groups. Other chemistries facilitating the covalent linkage between the nanoparticle 78 and the analyte binding receptor 6 or analyte equivalent residue 8 are intended to fall within the scope of this invention.

Finally, while many of the examples and embodiments are described in the context of glucose sensing, the present invention is applicable to sensing, sampling, measuring and/or analyzing analyte concentration whether or not the analyte is glucose. Such embodiments are merely exemplary. It is to be understood that other embodiments may be utilized, and changes may be made, without departing from the spirit or scope of the present invention as recited in the attached claims. As such, the foregoing description of the exemplary embodiments of the invention has been presented for the purposes of illustration and description. They are not intended to be exhaustive of, or to limit the invention to the precise forms disclosed. Many modifications and variations are possible in light of the above teaching. As such, the foregoing description of the exemplary embodiments of the invention has been presented for the purposes of illustration and description. It is intended that the scope of the invention be limited not to this detailed description, but rather by the claims appended hereto.

What is claimed is:

1. An analyte sensing device for sensing a concentration of analyte in a fluid, the analyte sensing device comprising:
a housing;
a first layer, disposed in the housing, having a first optical property that is responsive to the concentration of analyte in communication therewith, the first layer including:
a matrix having a plurality of first analyte equivalent residues disposed therein; and
a plurality of first analyte binding receptor molecules, wherein the first analyte binding receptor molecules are capable of reversibly binding with the first analyte equivalent residues and the analyte; and
a second layer, disposed in the housing, having at least one optical property that is insensitive to the concentration of analyte in communication therewith;
wherein the first optical property is a scattering of optical radiation incident on the first layer.

2. The analyte sensing device of claim 1 wherein the analyte is glucose.

3. The analyte sensing device of claim 1 wherein the housing includes a first portion that is permeable to the analyte and non-permeable to the first layer.

4. The analyte sensing device of claim 1 wherein the first portion of the housing is a membrane.

5. The analyte sensing device of claim 4 wherein the membrane is cellulose acetate and/or polysulphone.

6. The analyte sensing device of claim 1 wherein the first layer further includes at least one extra-matrix space disposed between the matrix and the housing.

7. The analyte sensing device of claim 1 wherein the housing further includes a reflecting portion disposed distal to a path of optical radiation that is incident on the first layer.

8. The analyte sensing device of claim 1 wherein the housing further includes a reflecting portion disposed distal to a path of optical radiation that is incident on the second layer.

9. The analyte sensing device of claim 1 wherein the housing further includes a reflecting portion disposed distal to a path of optical radiation that is incident on the first and second layers.

10. The analyte sensing device of claim 1 further including a third layer having at least one optical property that is responsive to the concentration of analyte in communication therewith, the third layer including:
a matrix having a plurality of second analyte equivalent residues disposed therein; and
a plurality of second analyte binding receptor molecules, wherein the second analyte binding receptor molecules are capable of reversibly binding with the second analyte equivalent residues and the analyte.

11. The analyte sensing device of claim 1 wherein the at least one optical property of the second layer provides a reference signal.

12. The analyte sensing device of claim 1 wherein the first layer further includes a plurality of nanoparticles which are attached to a plurality of the first analyte binding receptor molecules.

13. The analyte sensing device of claim 1 wherein the first layer further includes a plurality of nanoparticles which are attached to a plurality of the first analyte equivalent residues.

14. The analyte sensing device of claim 1 wherein the first layer further includes a plurality of nanoparticles which are attached to a plurality of the first analyte binding receptor molecules and a plurality of the first analyte equivalent residues.

15. An analyte sensing device for sensing a concentration of analyte in a fluid, the analyte sensing device comprising:
a housing having:
a first portion that is permeable to the analyte and non-permeable to a first layer; and
a reflecting portion;
the first layer, disposed in the housing, having a first optical property that is responsive to the concentration of analyte in communication therewith wherein the first optical property is a scattering of optical radiation incident on the first layer, the first layer including:
a matrix having a plurality of first analyte equivalent residues disposed therein; and
a plurality of first analyte binding receptor molecules, wherein the first analyte binding receptor molecules are capable of reversibly binding with the first analyte equivalent residues and the analyte; and
wherein the reflecting portion is disposed distal to a path of optical radiation that is incident on the first layer.

16. The analyte sensing device of claim 15 wherein the analyte is glucose.

17. The analyte sensing device of claim 15 wherein the housing includes a first portion that is permeable to the analyte.

18. The analyte sensing device of claim 17 wherein the first portion of the housing is a membrane.

19. The analyte sensing device of claim 18 wherein the membrane is cellulose acetate and/or polysulphone.

20. The analyte sensing device of claim 15 wherein the first layer further includes at least one extra-matrix space disposed between the matrix and the housing.

21. The analyte sensing device of claim 15 wherein the housing further includes a reflecting portion disposed distal to a path of optical radiation that is incident on the second layer.

22. The analyte sensing device of claim 15 further including a second layer having at least one optical property that is responsive to the concentration of analyte in communication therewith, the second layer including:
a matrix having a plurality of second analyte equivalent residues disposed therein; and
a plurality of second analyte binding receptor molecules, wherein the second analyte binding receptor molecules are capable of reversibly binding with the second analyte equivalent residues and the analyte.

23. The analyte sensing device of claim 15 wherein the first layer further includes a plurality of nanoparticles which are attached to a plurality of the first analyte binding receptor molecules.

24. The analyte sensing device of claim 15 wherein the first layer further includes a plurality of nanoparticles which are attached to a plurality of the first analyte equivalent residues.

25. The analyte sensing device of claim 15 wherein the first layer further includes a plurality of nanoparticles which are attached to a plurality of the first analyte binding receptor molecules and a plurality of the first analyte equivalent residues.

26. An analyte sensing system for sensing a concentration of analyte in a fluid, the analyte sensing system comprising:
a first device including:
a first layer having a first optical property that is responsive to the concentration of analyte in communication therewith wherein the first optical property is a scattering of optical radiation incident on the first layer, the first layer including:

a matrix having a plurality of first analyte equivalent residues disposed therein; and a plurality of first analyte binding receptor molecules, wherein the first analyte binding receptor molecules are capable of reversibly binding with the first analyte equivalent residues and the analyte; and a second device including a first layer having at least one optical property that includes a predetermined response to the concentration of analyte in communication therewith.

27. The analyte sensing system of claim 26 wherein the analyte is glucose.

28. The analyte sensing system of claim 26 wherein the first layer of the first device further includes at least one extra-matrix space disposed adjacent to the matrix.

29. The analyte sensing system of claim 26 wherein the first device further includes a housing having a reflecting portion disposed distal to a path of optical radiation that is incident on the first layer of the first device.

30. The analyte sensing system of claim 26 wherein the second device further includes a housing having a reflecting portion disposed distal to a path of optical radiation that is incident on the first layer of the second device.

31. The analyte sensing system of claim 26 wherein the at least one optical property of the first layer of the second device provides a reference signal.

32. The analyte sensing system of claim 26 wherein the at least one optical property of the first layer of the second device includes a predetermined response to the concentration of analyte in communication therewith over a first range of concentrations of analyte.

33. The analyte sensing system of claim 26 wherein the first layer of the first device further includes a plurality of nanoparticles that are attached to a plurality of the first analyte binding receptor molecules.

34. The analyte sensing system of claim 26 wherein the first layer of the first device further includes a plurality of nanoparticles that are attached to a plurality of the first analyte equivalent residues.

35. A method to detect the concentration of an analyte in a fluid using an analyte sensing device comprising (1) a first layer disposed within a housing, wherein the first layer exhibits at least one optical property that is responsive to the concentration of analyte in communication therewith, the first layer including a matrix having a plurality of analyte equivalent residues disposed therein, and a plurality of analyte binding receptor molecules, wherein the analyte binding receptor molecules are capable of reversibly binding with the analyte equivalent residues and the analyte, and (2) a second layer, disposed in the housing, having at least one optical property that is insensitive to the concentration of analyte in communication therewith, the method comprising:

placing the analyte sensing device in communication with the fluid;

providing incident optical radiation to the analyte sensing device;

receiving responsive optical radiation from the analyte sensing device;

determining the concentration of analyte by using (i) the responsive optical radiation to measure a change in scattering of optical radiation by the first layer and (ii) a response to the optical radiation by the second layer; and outputting data which is representative of the concentration of analyte.

36. The method of claim 35 further including analyzing the responsive optical radiation to detect fluorescence which depends at least partially on analyte-dependent optical properties.

37. The method of claim 35 wherein providing incident optical radiation to the analyte sensing device includes providing incident optical radiation to the analyte sensing device using an optical coherence tomography instrument.

38. The method of claim 35 further including analyzing the responsive optical radiation to determine a change in scattering of optical radiation by the first layer and wherein analyzing the responsive optical radiation includes using a mathematical analysis of one or more optical coherence tomography return signals of the responsive optical radiation.

39. The method of claim 35 wherein analyzing the responsive optical radiation to measure a change in scattering of optical radiation by the first layer includes measuring the transmission of optical radiation incident on the first layer to determine the scattering of optical radiation incident on the first layer.

40. The method of claim 35 further including measuring the at least one optical property of the second layer.

41. The method of claim 40 wherein the at least one optical property of the second layer provides a reference signal.

* * * * *